(12) United States Patent
Senouf et al.

(10) Patent No.: US 11,158,052 B2
(45) Date of Patent: Oct. 26, 2021

(54) SYSTEMS AND METHODS FOR ULTRASONIC IMAGING

(71) Applicant: Technion Research & Development Foundation Limited, Haifa (IL)

(72) Inventors: Ortal Senouf, Haifa (IL); Sanketh Vedula, Haifa (IL); Alexander Bronstein, Haifa (IL); Michael Zibulevsky, Jerusalem (IL); Grigoriy Zurakhov, Haifa (IL); Oleg Michailovich, Waterloo (CA)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 17/268,605

(22) PCT Filed: Aug. 14, 2019

(86) PCT No.: PCT/IL2019/050915
§ 371 (c)(1),
(2) Date: Feb. 16, 2021

(87) PCT Pub. No.: WO2020/035864
PCT Pub. Date: Feb. 20, 2020

(65) Prior Publication Data
US 2021/0256700 A1    Aug. 19, 2021

Related U.S. Application Data

(60) Provisional application No. 62/764,768, filed on Aug. 16, 2018.

(51) Int. Cl.
*G06T 7/00*     (2017.01)
*A61B 8/02*     (2006.01)
*A61B 8/08*     (2006.01)

(52) U.S. Cl.
CPC ............ *G06T 7/0014* (2013.01); *A61B 8/02* (2013.01); *A61B 8/5207* (2013.01);
(Continued)

(58) Field of Classification Search
None
See application file for complete search history.

(56) References Cited

U.S. PATENT DOCUMENTS

2009/0268952 A1* 10/2009 Schaffer ............... G06K 9/6217
                                                          382/128
2017/0143312 A1   5/2017 Hedlund et al.

FOREIGN PATENT DOCUMENTS

WO    WO 2018/048507    3/2018
WO    WO 2020/035864    2/2020

OTHER PUBLICATIONS

International Search Report and the Written Opinion dated Nov. 7, 2019 From the International Searching Authority Re. Application No. PCT/IL2019/050915. (10 Pages).
(Continued)

*Primary Examiner* — Matthew C Bella
*Assistant Examiner* — Brian D Shin

(57) ABSTRACT

There is provided an ultrasound device comprising: ultrasound transducer(s), memory storing code, hardware processor(s) coupled to the ultrasound transducer(s) and the memory for executing stored code comprising: activating the transducer(s) for simultaneously transmitting at least one line with a predefined focus width, and receiving an indication of a plurality of narrow-focused received lines, inputting the indication of the narrow-focused received lines into a convolutional neural network (CNN) trained on pairs of ultrasound imaging data capturing rapid motion of the certain tissue of sample patient(s), including a single-line ultrasound imaging data captured based on a single line in response to a transmitted single narrow-focused pulse, and
(Continued)

a multiple-line ultrasound imaging data captured based on receiving narrow-focused lines in response to simultaneously transmitted at least one line, outputting adjusted narrow-focused received lines, and computing an adjusted ultrasound image according to the adjusted narrow-focused received lines for presentation on a display.

20 Claims, 9 Drawing Sheets

(52) U.S. Cl.
CPC .............. *G06T 2207/10132* (2013.01); *G06T 2207/20081* (2013.01); *G06T 2207/20084* (2013.01); *G06T 2207/30048* (2013.01)

(56) References Cited

OTHER PUBLICATIONS

Rabinovich et al. "Multi-Line Acquisition With Minimum Variance Beamforming in Medical Ultrasound Imaging", IEEE Transactions on Ultrasonic, Ferroelectrics, and Frequency Control, 60(12): 2521-2531, Dec. 2013.

* cited by examiner

SYSTEMS AND METHODS FOR ULTRASONIC IMAGING

RELATED APPLICATIONS

This application is a National Phase of PCT Patent Application No. PCT/IL2019/050915 having International filing date of Aug. 14, 2019, which claims the benefit of priority under 35 USC § 119(e) of U.S. Provisional Patent Application No. 62/764,768 filed on Aug. 16, 2018. The contents of the above applications are all incorporated by reference as if fully set forth herein in their entirety.

BACKGROUND

The present invention, in some embodiments thereof, relates to signal processing and, more specifically, but not exclusively, to systems and methods for improving quality of ultrasound images.

Medical ultrasound is a wide-spread imaging modality due to its high temporal resolution, lack of harmful radiation and cost-effectiveness, which distinguishes it from other modalities such as MRI and CT.

High temporal resolution is highly desired in additional to spatial resolution for certain ultrasound examinations. For example, for investigating deformations at different stages of the cardiac cycle.

SUMMARY

According to a first aspect, an ultrasound device for imaging rapid motion of a certain tissue in a target patient, comprises: at least one ultrasound transducer, a memory storing code, at least one hardware processor coupled to the at least one ultrasound transducer and the memory for executing the stored code, the code comprising: code for activating the at least one ultrasound transducer for simultaneously transmitting at least one line with a predefined focus width, and receiving from the at least one ultrasound transducer an indication of a plurality of narrow-focused received lines in response to the transmitted at least one line, code for inputting the indication of the plurality of narrow-focused received lines into a convolutional neural network (CNN), wherein the CNN is trained on a training set comprising a plurality of pairs of ultrasound imaging data capturing rapid motion of the certain tissue of at least one sample patient, wherein each pair of the plurality of pairs of ultrasound imaging data includes a single-line ultrasound imaging data captured based on at least one ultrasound transducer receiving a single line in response to a transmitted single narrow-focused pulse, and a multiple-line ultrasound imaging data captured based on at least one ultrasound transducer receiving a plurality of narrow-focused lines in response to simultaneously transmitted at least one line with predefined focus width, and outputting by the CNN, a plurality of adjusted narrow-focused received lines, code for computing an adjusted ultrasound image according to the plurality of adjusted narrow-focused received lines, and code for outputting the adjusted ultrasound image for presentation on a display.

According to a second aspect, a method for imaging rapid motion of a certain tissue in a target patient, comprises: activating at least one ultrasound transducer for simultaneously transmitting at least one line with a predefined focus width, and receiving from the at least one ultrasound transducer an indication of a plurality of narrow-focused received lines in response to the transmitted at least one line, inputting the indication of the plurality of narrow-focused received lines into a convolutional neural network (CNN), wherein the CNN is trained on a training set comprising a plurality of pairs of ultrasound imaging data capturing rapid motion of the certain tissue of at least one sample patient, wherein each pair of the plurality of pairs of ultrasound imaging data includes a single-line ultrasound imaging data captured based on at least one ultrasound transducer receiving a single line in response to a transmitted single narrow-focused pulse, and a multiple-line ultrasound imaging data captured based on at least one ultrasound transducer receiving a plurality of narrow-focused lines in response to simultaneously transmitted at least one line with predefined focus width, and outputting by the CNN, a plurality of adjusted narrow-focused received line, computing an adjusted ultrasound image according to the plurality of adjusted narrow-focused received lines, and providing the adjusted ultrasound image for presentation on a display.

According to a third aspect, a system for training a CNN of an ultrasound device for imaging rapid motion of a certain tissue in a target patient, comprises: at least one ultrasound transducer, a memory storing code, at least one hardware processor coupled to the at least one ultrasound transducer and the memory for executing the stored code, the code comprising: code for activating the at least one ultrasound transducer for simultaneously transmitting at least one line with a predefined focus width, and receiving an indication of a plurality of narrow-focused received lines in response to the transmitted at least one line, code for creating a training dataset comprising a plurality of pairs of ultrasound imaging data capturing rapid motion of the certain tissue of at least one sample patient, wherein each pair of the plurality of pairs of ultrasound imaging data includes a single-line ultrasound imaging data captured based on at least one ultrasound transducer receiving a single line in response to a transmitted single narrow-focused pulse, and a multiple-line ultrasound imaging data captured based on at least one ultrasound transducer receiving a plurality of narrow-focused lines in response to simultaneously transmitted at least one line with predefined focus width, and code for training a CNN according to the training data, for outputting a plurality of adjusted narrow-focused received lines according to an input of the indication of the plurality of narrow-focused received lines.

At least some of the systems, methods, apparatus, and/or code instructions described herein address the technical problem of generating high frame rate ultrasound images, in particular, generating high frame rate ultrasound imaging with relatively low amount of artifacts.

The technical problem may relate to capturing high quality ultrasound images of tissue moving within a patient (e.g., beating heart). Generating high quality images of rapidly moving organs requires high frame rate ultrasonic imaging. Increasing the frame rate is a major challenge in two dimensional (2D) and/or three dimensional (3D) and/or four dimensional (4D) ultrasonic image, in particular for imaging rapid motion, for example, the beating heart. For a given angular sector size and acquisition depth, the frame rate is limited by the speed of sound in soft tissues (about 1540 meters/second). The frame rate depends on the number of transmitted beams needed to cover the field of view. The frame rate may be increased by lowering the number of the transmitted events.

At least some of the systems, methods, apparatus, and/or code instructions described herein address the technical problem of improving image quality of ultrasound images generated by an MLA set-up (also referred to as parallel receive beamforming (PRB)), in particular, reducing and/or correcting artifacts introduced into the ultrasound image resulting from the MLA set-up. The technical problem may relate to capturing high quality ultrasound images of tissue moving within a patient (e.g., beating heart) using the MLA set-up.

At least some of the systems, methods, apparatus, and/or code instructions described herein address the technical problem of improving image quality of ultrasound images generated by an MLT set-up, in particular, reducing and/or correcting artifacts introduced into the ultrasound image resulting from the MLT set-up. While MLT reduces the acquisition time, it comes at the expense of a heavy loss of contrast due to the interactions between the beams (i.e., cross-talk artifacts). The technical problem may relate to capturing high quality ultrasound images of tissue moving within a patient (e.g., beating heart) using the MLT set-up.

At least some of the systems, methods, apparatus, and/or code instructions described herein address the technical problem of improving image quality of ultrasound images generated by an MLT-MLA set-up, in particular, reducing and/or correcting artifacts introduced into the ultrasound image resulting from the MLT-MLA set-up. The technical problem may relate to capturing high quality ultrasound images of tissue moving within a patient (e.g., beating heart) using the MLT-MLA set-up.

In a further implementation form of the first, second, and third aspects, the simultaneously transmitted at least one line with predefined focus width is a single wide-focus line.

In a further implementation form of the first, second, and third aspects, the plurality of received lines received in response to the single wide-focused line are an odd number for increasing the frame rate of the adjusted ultrasound images by the odd number.

In a further implementation form of the first, second, and third aspects, the simultaneously transmitted at least one line with predefined focus width comprises a plurality of narrow-focused lines.

In a further implementation form of the first, second, and third aspects, the simultaneously transmitted at least one line with predefined focus width comprises a plurality of wide-focused lines.

In a further implementation form of the first, second, and third aspects, the at least one ultrasound transducer comprises a plurality of elements arranged as a phased array, wherein the indication of the plurality of narrow-focused received lines inputted into the CNN comprises raw in-phase and quadrature (I/Q) output of each of the plurality of elements, and the plurality of adjusted narrow-focused received lines outputted by the CNN comprise adjusted I/Q outputs for input into a process that generates ultrasound images based on I/Q outputs of elements.

In a further implementation form of the first, second, and third aspects, the CNN comprises a plurality of interpolation layers followed by an apodization layer.

In a further implementation form of the first, second, and third aspects, the plurality of interpolation layers comprise a plurality of convolutional layers arranged as a downsampling track followed by an upsampling track, wherein a plurality of skip connections connect each interpolation layer of the downsampling track to a corresponding interpolayer layer of the upsampling track.

In a further implementation form of the first, second, and third aspects, the downsampling track comprises a plurality of average pooling layers and the upsampling track comprises a plurality of strided convolutions.

In a further implementation form of the first, second, and third aspects, the at least one ultrasound transducer comprises a plurality of elements arranged as a phased array, wherein the indication of the plurality of narrow-focused received lines inputted into a first layer of the plurality of interpolation layers of the CNN comprises raw I/Q output of each of the plurality of elements.

In a further implementation form of the first, second, and third aspects, the at least one ultrasound transducer comprises a plurality of elements arranged as a phased array, wherein the apodization layer comprising a convolutional layer for each of a plurality of channels corresponding to each of the plurality of elements, and wherein computed point-wise convolutions are added to the weights of the convolution.

In a further implementation form of the first, second, and third aspects, the at least one ultrasound transmitter transmits a plurality of lines, wherein each lines of the plurality of transmitted lines comprise a respective single wide-focused line.

In a further implementation form of the first, second, and third aspects, the at least one ultrasound transducer comprises a plurality of elements arranged as a phased array, wherein the CNN comprises a plurality of interpolation layers followed by an apodization layer comprising a convolutional layer for each of a plurality of channels corresponding to each of the plurality of elements, wherein the weights of each of the plurality of channels are initialized with a Hann window.

In a further implementation form of the first, second, and third aspects, the CNN is trained by computing a discrepancy between the plurality of adjusted narrow-focused received lines computed by the CNN and the single-line imaging data denoting ground truth, and minimizing the discrepancy according to code for an optimizer.

In a further implementation form of the first, second, and third aspects, the discrepancy is computed according to L1 norm training loss.

In a further implementation form of the first, second, and third aspects, the single-line imaging data of each pair of the training dataset is obtained by ultrasound imaging of a sample individual, and the multi-line imaging data corresponding to the single-line imaging data denotes phantom data computed from the single-line imaging data by decimating the received pre-beamformed data.

In a further implementation form of the first, second, and third aspects, the single-line imaging data of each pair of the training dataset is obtained by ultrasound imaging of a sample individual, and the multi-line imaging data corresponding to the single-line imaging data denotes phantom data computed from the single-line imaging data by summation of the received pre-beamformed data.

In a further implementation form of the first, second, and third aspects, the system and/or method further comprise creating the training dataset, and training the CNN according to the training data.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
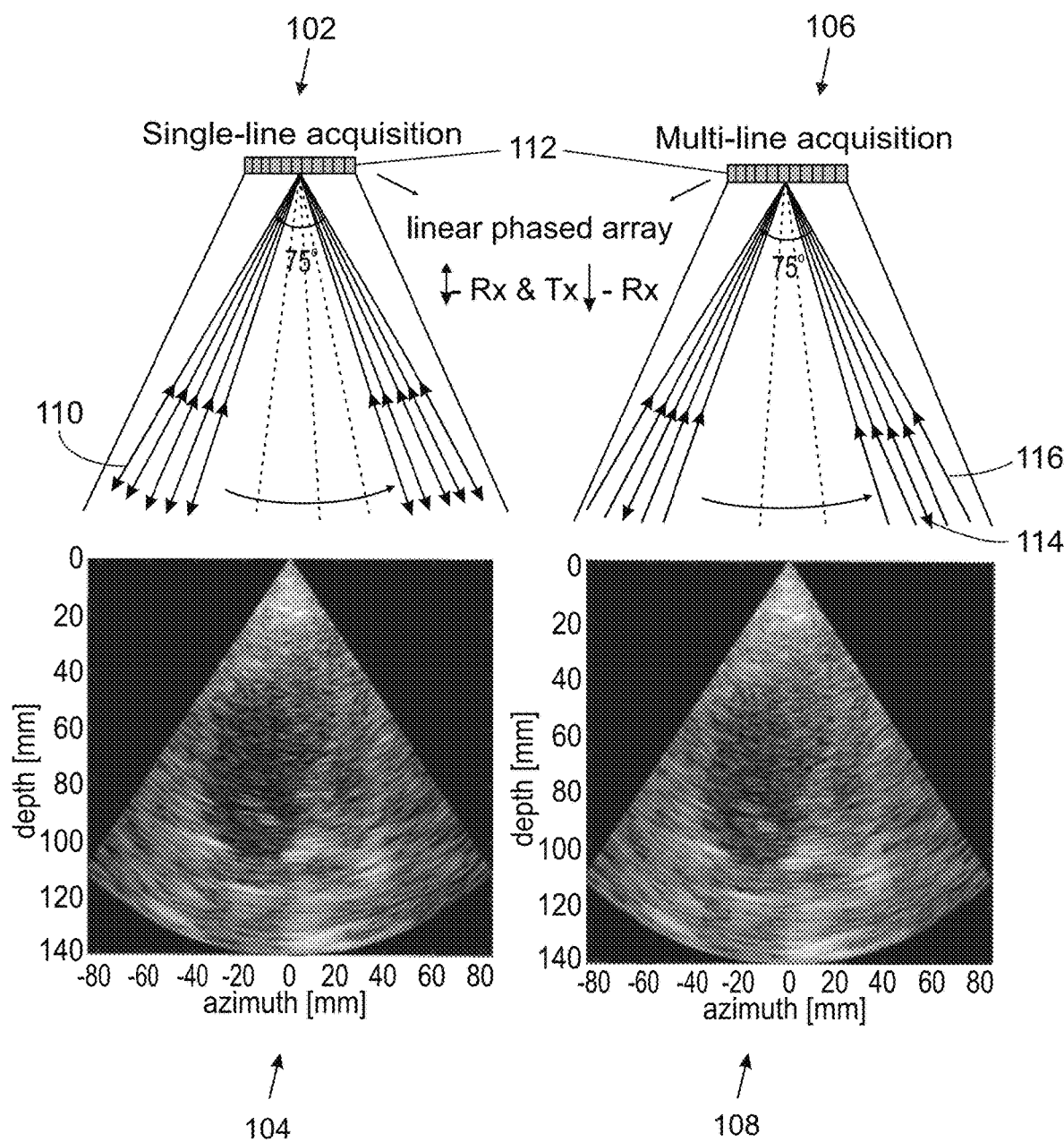
FIG. 1A is a schematic depicting a set-up for single-line acquisition (SLA) and multi-line acquisition (MLA), to help better understand some embodiments of the present invention.

The present invention, in some embodiments thereof, relates to signal processing and, more specifically, but not exclusively, to systems and methods for improving quality of ultrasound images.

As used herein, the term SLA means single-line acquisition, and the term MLA means multi-line acquisition. The term received line may refer to an implementation based on SLA. The term received lines may refer to an implementation based on MLA.

As used herein, the term SLT means single-line transmission, and the term MLT means multi-line transmission. The term transmitted line may refer to an implementation based on SLT. The term transmitted lines may refer to an implementation based on MLT.

As used herein, the term MLT-MLA or MLA-MLT refers to a combination of MLT and MLA, where multiple individual lines are simultaneously transmitted, and multiple lines are received in response to each individual line.

It is noted that in an exemplary application, imaging is performed on a rapidly moving organ such as the heart. However, at least some of the US device, systems, methods, and/or code instructions described herein may be used to image slowly moving tissues and/or non-moving tissues of the target patient, for example, abdominal structures (e.g., liver, pancreas, gall bladder), brain, a fetus, uterine tissues, pelvic tissues, and/or urinary system tissues (e.g., kidney, bladder, urinary ducts).

An aspect of some embodiments of the present invention relates to an ultrasound device (i.e., an apparatus), systems, methods, and/or code instructions (e.g., stored on a data storage device, executable by one or more hardware processors) for ultrasound imaging of a target tissue(s) of a target patient, optionally target tissue(s) undergoing rapid motion, for example, the heart and/or sub-structures thereof such as valves, atria, and/or ventricles. Ultrasound transducer(s) are activated for simultaneously transmitting one or more line(s) with a predefined focus width. The one or more lines may be transmitted based on MLA (i.e., a single transmitted line), MLT (i.e., multiple lines), and/or combined MLT-MLA (i.e., a set of multiple single transmitted lines). An indication of multiple narrow-focused received lines are obtained from the ultrasound transducer(s) in response to the transmitted one or more lines. The received lines may be according to MLA (i.e., multiple received lines in response to the single transmitted line), MLT (i.e., multiple lines received in response to multiple transmitted lines), and/or combined MLT-MLA (i.e., multiples lines received in response to each single line of a set of multiple single transmitted lines). The received indication of the narrow-focused received lines is inputted into a convolutional neural network (CNN). The CNN is trained on a training dataset that includes pairs of ultrasound imaging data, capturing rapid motion of target tissue of sample patient(s). Each of the pairs of ultrasound imaging data includes a single-line ultrasound imaging data captured based on ultrasound transducer(s) receiving a single line in response to a transmitted single narrow-focused pulse (e.g., based on SLT and SLA), and a multiple-line ultrasound imaging data captured based on ultrasound transducer(s) receiving multiple narrow-focused lines in response to simultaneously transmitted line(s) with predefined focus width (e.g., based on MLT, MLA, or MLT-MLA). The CNN outputs adjusted narrow-focused received lines. An adjusted ultrasound image is computed (e.g., reconstructed) according to the adjusted narrow-focused received lines. The adjusted ultrasound image is provided for presentation on a display.

An aspect of some embodiments of the present invention relates to an ultrasound device (i.e., an apparatus), systems, methods, and/or code instructions (e.g., stored on a data storage device, executable by one or more hardware processors) for training a CNN associated with an ultrasound device for imaging rapid motion of a target tissue(s) in a target patient. Ultrasound transducer(s) are activated for simultaneously transmitting one or more line(s) with a predefined focus width. The one or more lines may be transmitted based on SLT, (i.e., a single transmitted), or MLT (i.e., multiple lines). An indication of multiple narrow-focused received lines are obtained from the ultrasound transducer(s) in response to the transmitted one or more lines. The received lines may be according to SLT-SLA (i.e., the single line received in response to a single transmission), SLT-MLA (i.e., multiple received lines in response to the single transmitted line), MLT-SLA (i.e., multiple lines received in response to multiple transmitted lines), and/or combined MLT-MLA (i.e., multiples lines receives in response to each single line of a set of multiple single transmitted lines). A training dataset is created, where the training dataset includes pairs of ultrasound imaging data capturing rapid motion of the target tissue(s) of respective sample patients. Each pair of ultrasound imaging data includes a single-line ultrasound imaging data captured based on ultrasound transducer(s) receiving a single line in response to a transmitted single narrow-focused pulse (e.g., based on SLT-SLA), and a multiple-line ultrasound imaging data captured based on ultrasound transducer(s) receiving multiple narrow-focused lines in response to simultaneously transmitted line(s) with predefined focus width (e.g., based on MLT-SLA, SLT-MLA, or MLT-MLA). The CNN is trained according to the training imaging data, where the received single line in response to the transmitted single narrow-focused pulse denotes the ground truth, and the multiple-line ultrasound imaging data denotes the input. The CNN is trained to output multiple adjusted narrow-focused received lines according to an input of the indication of the narrow-focused received lines. Conceptually, the CNN corrects the output of the transducer(s) when receiving the narrow-focused received lines, to generate a higher quality ultrasound image that is more similar (e.g., higher correlation) and/or higher quality (e.g., less artifacts) to the ground truth image that would otherwise be reconstructed based on single received lines, in comparison to an un-adjusted image that would otherwise be reconstructed based on the un-adjusted output of the transducer(s) in response to multiple received lines.

At least some of the systems, methods, apparatus, and/or code instructions described herein address the technical problem of generating high frame rate ultrasound images, in particular, generating high frame rate ultrasound imaging with relatively low amount of artifacts.

The technical problem may relate to capturing high quality ultrasound images of tissue moving within a patient (e.g., beating heart). Generating high quality images of rapidly moving organs requires high frame rate ultrasonic imaging. Increasing the frame rate is a major challenge in two dimensional (2D) and/or three dimensional (3D) and/or four dimensional (4D) ultrasonic image, in particular for imaging rapid motion, for example, the beating heart. For a given angular sector size and acquisition depth, the frame rate is limited by the speed of sound in soft tissues (about 1540 meters/second). The frame rate depends on the number of transmitted beams needed to cover the field of view. The frame rate may be increased by lowering the number of the transmitted events.

At least some of the systems, methods, apparatus, and/or code instructions described herein address the technical problem of improving image quality of ultrasound images generated by an MLA set-up (also referred to as parallel receive beamforming (PRB)), in particular, reducing and/or correcting artifacts introduced into the ultrasound image resulting from the MLA set-up. The technical problem may relate to capturing high quality ultrasound images of tissue moving within a patient (e.g., beating heart) using the MLA set-up.

At least some of the systems, methods, apparatus, and/or code instructions described herein address the technical problem of improving image quality of ultrasound images generated by an MLT set-up, in particular, reducing and/or correcting artifacts introduced into the ultrasound image resulting from the MLT set-up. While MLT reduces the acquisition time, it comes at the expense of a heavy loss of contrast due to the interactions between the beams (i.e., cross-talk artifacts). The technical problem may relate to capturing high quality ultrasound images of tissue moving within a patient (e.g., beating heart) using the MLT set-up.

At least some of the systems, methods, apparatus, and/or code instructions described herein address the technical problem of improving image quality of ultrasound images generated by an MLT-MLA set-up, in particular, reducing and/or correcting artifacts introduced into the ultrasound image resulting from the MLT-MLA set-up. The technical problem may relate to capturing high quality ultrasound images of tissue moving within a patient (e.g., beating heart) using the MLT-MLA set-up.

Reference is first made to FIG. 1A, which is a schematic depicting a set-up for single-line acquisition (SLA) 102, an ultrasound image 104 acquired based on set-up for single-line acquisition, a set-up for multi-line acquisition (MLA) 106, and an ultrasound image 108 acquired based on set-up of multi-line acquisition 106, to help better understand some embodiments of the present invention.

It is noted that the SLA and MLA processes described with reference to FIG. 1A, are exemplary and not necessarily limiting, as some implementations of the systems, methods, apparatus, and/or code instructions described herein may relate to other implementations based on a single transmitted line and reception of multiple lines.

MLA is one of several ways for increasing the frame rate of ultrasound imaging. MLA, which is one of the most commonly used techniques, is implemented in many ultrasound scanners, and is described in additional detail, for example, with reference to Shattuck, D. P., Weinshenker, M. D., Smith, S. W., von Ramm, O. T.: *Explososcan: A parallel processing technique for high speed ultrasound imaging with linear phased arrays. Acoustical Society of America Journal* 75 (April 1984) 1273-1282 and Ramm, O. T. V., Smith, S. W., Pavy, H. G.: *High-speed ultrasound volumetric imaging system. ii. parallel processing and image display. IEEE Transactions on Ultrasonics, Ferroelectrics, and Frequency Control* 38(2) (March 1991) 109-115. MLA is often referred to as parallel receive beamforming (PRB), described in additional detail, for example, with reference to Hergum, T., Bjastad, T., Kristoffersen, K., Torp, H.: *Parallel beamforming using synthetic transmit beams. IEEE transactions on ultrasonics, ferroelectrics, and frequency control* 54(2) (2007) 271-280.

In SLT-SLA, a narrow-focused pulse (one marked as 110 for simplicity and clarity of explanation) is transmitted by introducing transmit time delays through a linear phased array 112 of acoustic transducer elements. Upon reception, the obtained signal is dynamically focused along the receive (Rx) direction which is identical to the transmit (Tx) direction. The spatial region of interest is raster scanned line-by-line to obtain an ultrasound image (e.g., US image 104 captured by SLA set-up 102).

As discussed herein, a large number of pulses transmitted sequentially results in a low frame rate and renders SLT-SLA inadequate for imaging applications such as cardiovascular imaging, where a high frame rate is desired, for example, for quantitative analysis or during stress tests. Moreover, SLT-SLA is inadequate for scanning large fields of view in real time 2D and/or 3D imaging application.

MLA was designed in an attempt to overcome the frame rate problem described herein. In SLT-MLA set-up 106, US phased array 112 transmit a weakly focused beam (one transmit beam 114 shown for simplicity and clarity of explanation) that provides a sufficiently wide coverage for a high number of received lines (one received line 116 shown for simplicity and clarity of explanation). On the receiver side, m lines are constructed from the data acquired from each transmit event, thereby increasing the frame rate by m (the latter number is usually referred to as the MLA factor). Set-up 106 depicts 5-MLA, where 5 Rx lines 116 are constructed per each Tx 114, increasing the frame rate by the factor of 5.

As the Tx 114 and Rx 116 are no longer aligned in the MLA mode of set-up 106, the two-way beam profile is shifted towards the original transmit direction, making the lateral sampling irregular, as described in additional detail, for example, with reference to Hergum, T., Bjastad, T., Kristoffersen, K., Torp, H.: *Parallel beamforming using synthetic transmit beams. IEEE transactions on ultrasonics, ferroelectrics, and frequency control* 54(2) (2007) 271-280. The beam warping effect causes sharp lateral discontinuities that are manifested as block artifacts in the image domain. US image 108 created by MLA set-up 106 depicts block artifacts in the ultrasound images, which tend to be more obvious when the number of transmit events decreases. Lateral block artifacts are seen in US image 108 along the lateral direction. Apart from beam warping, there are two other effects caused by the transmit-receive misalignment: skewing, where shape of the two-way beam profile becomes asymmetric, and gain variation, where the outermost lines inside the group have a lower gain than the innermost lines, which are described in additional detail, for example, with reference to Bjastad, T., Aase, S. A., Torp, H.: *The impact of aberration on high frame rate cardiac b-mode imaging. IEEE Transactions on Ultrasonics Ferroelectrics and Frequency Control* 54(1) (2007) 32. It is noted that for comparison, US image 104 created by SLA set-up 102 does not include the MLA artifacts that appear in US image 108 created by MLA set-up 106.

At least some of the systems, methods, apparatus, and/or code instructions described herein improve the quality of US images generated by an MLA set-up according to a CNN that is trained on a training dataset that includes US images captured on sample patients by a SLA set-up, for example, in comparison to approaches of other systems and methods that are designed to decrease MLA artifacts.

Using standard methods, ultrasound images created from data generated from the MLA set-up suffers from block-like artifacts, reduced lateral resolution, and/or reduced contrast, for example, as described with reference to Rabinovich, A., Friedman, Z., Feuer, A.: Multi-line acquisition with minimum variance beamforming in medical ultrasound imaging. IEEE transactions on ultrasonics, ferroelectrics, and frequency control 60(12), 2521-2531 (2013). At least some of the systems, methods, apparatus, and/or code instructions described herein reduce or prevent such block-like artifacts, reduced lateral resolution, and/or reduced contrast. At least some of the systems, methods, apparatus, and/or code instructions described herein generate improved quality ultrasound images in comparison to the other methods, that are based on alternative approaches that do not use an CNN trained on SLA data (which represent the highest quality ultrasound images that are achievable), where the improved quality ultrasound images have relatively reduced artifacts, and/or relatively improved lateral resolution and/or relatively improved contrast in comparison to the other non-CNN methods. At least some of the systems, methods, apparatus, and/or code instructions described herein generate ultrasound images closely correlated to images created based on SLA data (i.e., baseline of high quality ultrasound images) that are outputted by the trained CNN described herein.

Examples of other approaches include:

Transmit sinc apodization, described with reference to Augustine, L. J.: High resolution multiline ultrasonic beamformer (Feb. 24, 1987) U.S. Pat. No. 4,644,795.

Dynamic steering described with reference to Thiele, K. E., Brauch, A.: Method and apparatus for dynamically steering ultrasonic phased arrays (Jun. 21, 1994) U.S. Pat. No. 5,322,068.

Incoherent interpolation described with reference to Holley, G. L., Guracar, I. M.: Ultrasound multi-beam distortion correction system and method (Jul. 14, 1998) U.S. Pat. No. 5,779,640.

A method applied after envelope detection described with reference to Liu, D. D., Lazenby, J. C., Banjanin, Z., McDermott, B. A.: System and method for reduction of parallel beamforming artifacts (Sep. 10, 2002) U.S. Pat. No. 6,447,452.

Coherence counterpart method applied before envelope detection described with reference to Wright, J. N., Maslak, S. H., Finger, D. J., Gee, A.: Method and apparatus for coherent image formation (Apr. 29, 1997) U.S. Pat. No. 5,623,928.

The synthetic transmit beamforming (STB) method, described with reference to Hergum, T., Bjastad, T., Kristoffersen, K., Torp, H.: *Parallel beamforming using synthetic transmit beams. IEEE transactions on ultrasonics, ferroelectrics, and frequency control* 54(2) (2007) 271-280, creates synthetic Tx lines by coherently interpolating information received from each two adjacent Tx events in intermediate directions.

At least some of the systems, methods, apparatus, and/or code instructions described herein improve image quality of images acquired based on an MLA set-up that implements a defined decimation rate, referred to as MLA factor (e.g., even or odd, for example, 4, 5, 6, 7 or other numbers; sometimes denoted herein as m). At least some of the systems, methods, apparatus, and/or code instructions described herein are data adaptive that are adjusted according to the decimation rate, regardless of the value of the MLA factor and/or regardless if the MLA factor is even or odd. In contrast, other MLA image methods with focused beams are designed to operate on a predefined number of Rx lines per each Tx event. For example, an even number of 2 or 4 in cases without overlap, or 4, 6, or 8 lines (i.e., even number) in the presence of overlaps from adjacent transmissions, in order to perform the correction, for example, as described with reference to Hergum, T., Bjastad, T., Kristoffersen, K., Torp, H.: *Parallel beamforming using synthetic transmit beams. IEEE transactions on ultrasonics, ferroelectrics, and frequency control* 54(2) (2007) 271-280, Bjastad, T., Aase, S. A., Torp, H.: *The impact of aberration on high frame rate cardiac b-mode imaging. IEEE Transactions on Ultrasonics Ferroelectrics and Frequency Control* 54(1) (2007) 32, and/or Rabinovich, A., Friedman, Z., Feuer, A.: *Multi-line acquisition with minimum variance beamforming in medical ultrasound imaging. IEEE transactions on ultrasonics, ferroelectrics, and frequency control*

60(12) (2013) 2521-2531. Such other methods perform constant correction, for example by creating eight lines with overlaps to provide an effective frame rate increase by a factor of 4, in comparison to at least some of the systems, methods, apparatus, and/or code instructions described herein that adaptively adjusts the increased frame rate according to the number of added lines.

Figure 1B:
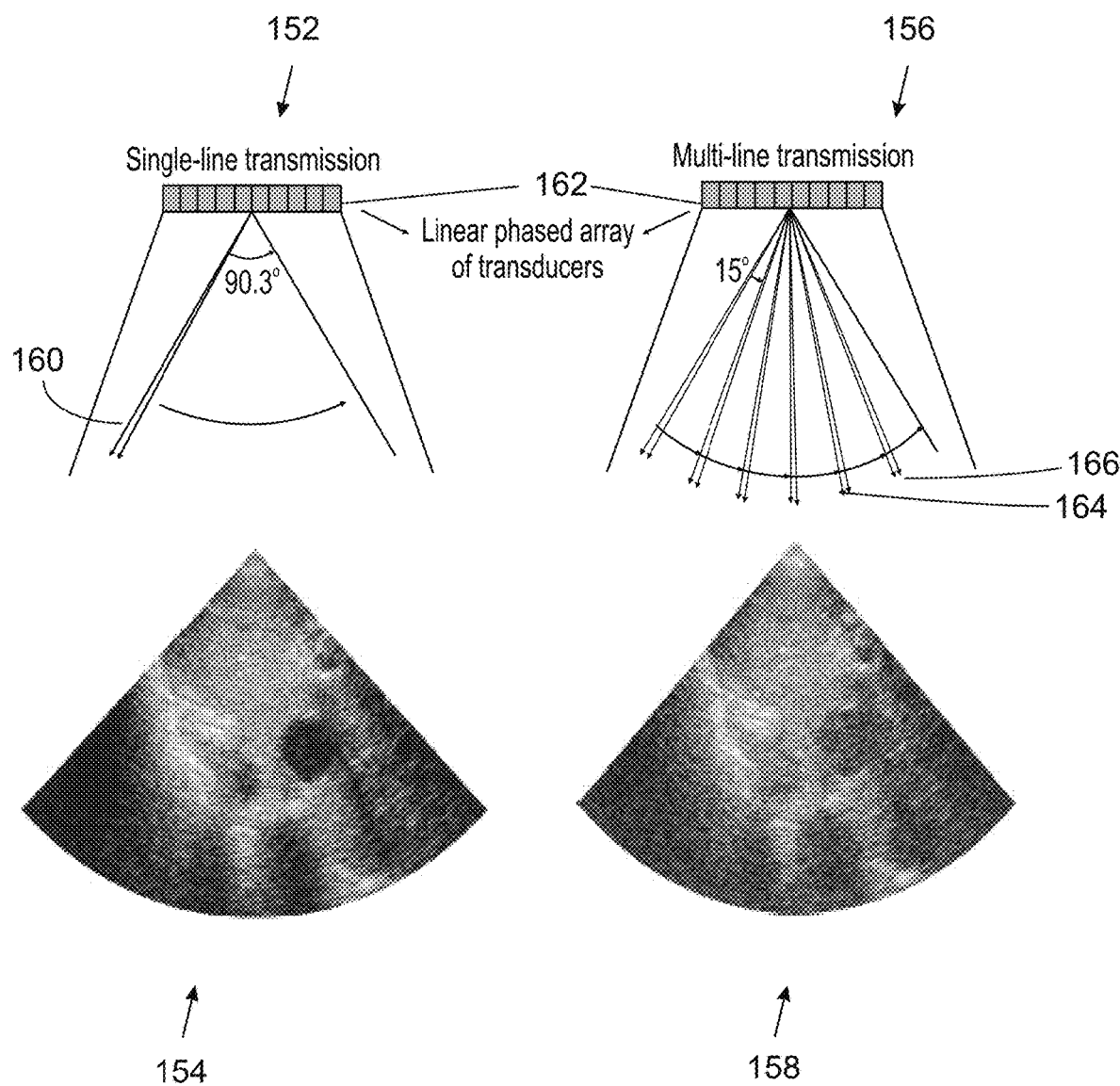
FIG. 1B is a schematic depicting a set-up for single-line transmission (SLT) and multi-line transmission (MLT), to help better understand some embodiments of the present invention.

Reference is now made to FIG. 1B, which is a schematic depicting a set-up for single-line transmission (SLT) 152, an ultrasound image 154 acquired based on set-up for SLT, a set-up for multi-line transmission (MLT) 156, and an ultrasound image 158 acquired based on the set-up of MLT 156, to help better understand some embodiments of the present invention.

In SLT, a single narrow-focused pulse (one marked as 160 for simplicity and clarity of explanation) is transmitted by introducing transmit time delays through a linear phased array 162 of acoustic transducer elements. Upon reception, the obtained signal is dynamically focused along the receive (Rx) direction which is identical to the transmit (Tx) direction. The spatial region of interest is raster scanned line-byline to obtain an ultrasound image (e.g., US image 154 captured by SLT set-up 152).

MLT is based on a simultaneous transmission of multiple number of narrow beams (two beams 164 and 166 marked for clarity of explanation) focused in different directions. MLT is described in additional detail, for example, with reference to Mallart, R., Fink, M.: Improved imaging rate through simultaneous transmission of several ultrasound beams. In: New Developments in Ultrasonic Transducers and Transducer Systems. vol. 1733, pp. 120-131. International Soc. for Optics and Photonics (1992) and Drukarev, A., Konstantinides, K., Seroussi, G.: *Beam transformation techniques for ultrasonic medical imaging. IEEE trans. on ultrasonics, ferroelectrics, and frequency control* 40(6), 717-726 (1993).

It is noted that in some cases (e.g., as described in the Experiment section), a limitation is placed on the number of simultaneous pulses and their separation, for example, for simulation, a 6 MLT setup is depicted in which 6 pulses are simultaneously transmitted, separated by 15 degrees. Since data acquired is in a tissue harmonic mode, the limitation of 15 degrees hold for this mode. However, the systems, methods, apparatus, and/or code instructions descried herein based on correction using trained CNN(s) is more general and may be extended to first-harmonic mode where the 15 degrees constraint no longer holds. Such extension may lead to extra orders of speed-up.

In comparing US image 158 produce by MLT setup 156 with US image 154 produced by SLT set up 152, a severe drop in contrast is observed in US image 158.

It is noted that the SLT and MLT processes described with reference to FIG. 1B, are exemplary and not necessarily limiting, as some implementations of the systems, methods, apparatus, and/or code instructions described herein may relate to other implementations based on a multiple transmitted lines and reception of multiple lines.

At least some of the systems, methods, apparatus, and/or code instructions described herein address the technical problem of improving utilization of ultrasound images acquired from an MLT setup in clinical practice. MLT suffers from a high energy content due to the simultaneous transmission, making it impractical or less practical clinically. Clinical use mandates the use of lower excitation voltage in real MLT, implemented in a standard way due to patient safety considerations, which affect the generation of the tissue harmonic and signal-to-noise ratio (SNR). Therefore, MLT use is partially limited clinically due to low quality US images, since generation of higher US images would violate clinical guidelines. Additional details of this technical problem are described with reference to Santos, P., Tong, L., Ortega, A., L_vstakken, L., Samset, E., Dhooge, J.: *Acoustic output of multi-line transmit beamforming for fast cardiac imaging: A simulation study. IEEE trans. on ultrasonics, ferroelectrics, and frequency control* 62(7), 1320-1330 (2015). At least some of the systems, methods, apparatus, and/or code instructions described herein increase the scope of use of MLT based imaging in clinical practice based on the trained CNN described herein. The trained CNN described herein may improve the quality of the ultrasound images generated based on image data acquired by MLT, even in clinical scenarios in which only relatively lower energies are allowed. It is noted that the trained CNN may improve the quality of ultrasound images captured by alternatively implementations of MLT (e.g., as described by Santos et al.) which are designed to provide a safer application of MLT within safety guidelines. The CNN described herein may increase the quality of images, independently of the selected number of simultaneous transmissions in the tissue harmonic mode, for example, up to 6 MLT.

Images created using standard methods based on the MLT set-up suffer from cross-talk artifacts on both the transmit and receive, caused by the interaction between the beams, for example, as described with reference to Tong, L., Gao, H., D'hooge, J.: *Multi-transmit beam forming for fast cardiac imaging-a simulation study. IEEE trans. on ultrasonics, ferroelectrics, and frequency control* 60(8), 1719-1731 (2013) and Tong, L., Ramalli, A., Jasaityte, R., Tortoli, P., D'hooge, J.: *Multi-transmit beam forming for fast cardiac imaging experimental validation and in vivo application. IEEE transactions on medical imaging* 33(6), 1205-1219 (2014). At least some of the systems, methods, apparatus, and/or code instructions described herein improve the quality of US images generated by the MLT set-up, by the trained CNN describe herein that corrects cross-talk artifacts and/or reduces the effects of cross-talk artifacts on the quality of the final reconstructed image. The use of the trained CNN described herein is different than other approaches to tackle the problem of cross-talk artifacts of ultrasound images based on the MLT set-up. For example: traditional approaches tackle the cross-talk artifacts by performing a linear or non-linear processing of a time-delayed element-wise data to reconstruct each pixel in the image. Some other approaches, none of which are based on a trained CNN as described herein, are now described in detail:

Approaches based on constant apodization, described with reference to Tong, L., Gao, H., D'hooge, J.: *Multi-transmit beam forming for fast cardiac imaging-a simulation study. IEEE trans. on ultrasonics, ferroelectrics, and frequency control* 60(8), 1719-1731 (2013) and Tong, L., Ramalli, A., Jasaityte, R., Tortoli, P., D'hooge, J.: *Multi-transmit beam forming for fast cardiac imaging experimental validation and in vivo application. IEEE transactions on medical imaging* 33(6), 1205-1219 (2014).

Approaches based on adaptive apodization, described with reference to Rabinovich, A., Feuer, A., Friedman, Z.: *Multi-line transmission combined with minimum variance beamforming in medical ultrasound imaging. IEEE trans. on ultrasonics, ferroelectrics, and frequency control* 62(5), 814-827 (2015) and Zurakhov, G., Tong, L., Ramalli, A., Tortoli, P., Dhooge, J., Friedman, Z., Adam, D.: *Multi line transmit beamform-* ing combined with adaptive apodization. *IEEE Trans. on Ultrasonics, Ferroelectrics, and Frequency Control* (2018).

Approaches based on allocating different frequency bands to different transmissions, described with reference to Demi, L., Verweij, M., Van Dongen, K. W.: *Parallel transmit beamforming using orthogonal frequency division multiplexing applied to harmonic imaging-a feasibility study. IEEE trans. on ultrasonics, ferroelectrics, and frequency control* 59(11)(2012) and Demi, L., Ramalli, A., Giannini, G., Mischi, M.: In vitro and in vivo tissue harmonic images obtained with parallel transmit beamforming by means of orthogonal frequency division multiplexing. *IEEE trans. on ultrasonics, ferroelectrics, and frequency control* 62(1), 230-235 (2015).

An approach based on using a tissue harmonic mode, described with reference to Prieur, F., Denarie, B., Austeng, A., Torp, H.: *Correspondence-multi-line transmission in medical imaging using the second-harmonic signal. IEEE trans. on ultrasonics, ferroelectrics, and frequency control* 60(12), 2682-2692 (2013).

An approach based on filtered delay-multiply-and-sum beamforming (F-DMAS), described with reference to Matrone, G., Savoia, A. S., Caliano, Gi. and Magenes, G.: *The delay multiply and sum beamforming algorithm in ultrasound b-mode medical imaging. IEEE trans. on medical imaging* 34(4), 940-949 (2015), proposed in the context of MLT, as described with reference to Matrone, G., Ramalli, A., Savoia, A. S., Tortoli, P., Magenes, G.: *High frame-rate, high resolution ultrasound imaging with multi-line transmission and filtered-delay multiply and sum beamforming. IEEE trans. on medical imaging* 36(2), 478-486 (2017).

An approach based on short-lag F-DMAS for MLT described with reference to Matrone, G., Ramalli, A.: *Spatial coherence of backscattered signals in multi-line transmit ultrasound imaging and its effect on short-lag filtered-delay multiply and sum beamforming. Applied Sciences* 8(4), 486 (2018).

By using a simulated 2-MLT, Prieur, F., Denarie, B., Austeng, A., Torp, H.: *Correspondence-multi-line transmission in medical imaging using the second-harmonic signal. IEEE trans. on ultrasonics, ferroelectrics, and frequency control* 60(12), 2682-2692 (2013) demonstrated that the tissue harmonic imaging mode provides images with a lower transmit cross-talk artifact as compared to the fundamental harmonic imaging. However, the receive cross-talk artifact still requires correction. In the experiments described with reference to the Examples section below, Inventors demonstrate that similarly to the fundamental harmonic, the cross-talk is more severe in the tissue harmonic mode for higher MLT configurations, which is manifested by a lower contrast.

It is noted that the systems, methods, apparatus, and/or code instructions described herein are not necessarily limited to only second harmonic MLT correction. Correction may be applied to MLT first harmonic imaging. To perform first harmonic correction, the CNN(s) may be trained accordingly.

When the features related to by the systems, methods, apparatus, and/or code instructions described herein are taken as a whole, the combination of the features amounts to significantly more than a simple mathematical calculation of an ultrasound image. The systems, methods, apparatus, and/or code instructions described herein do not merely relate to mathematical computations, but relate to the particular way in which the CNN having a particular architecture is trained using SLA and MLA and/or SLT and MLT data, and/or the particular architecture of the trained CNN which is designed for adjusting lines obtained by a MLA and/or MLT set-up to achieve image quality comparable to ultrasound images that would otherwise be obtained by SLA and/or SLT data (however it is noted that as discussed herein, the SLA and/or SLT data is for comparison purposes but not clinically practical since SLA and/or SLT images cannot feasibly be generated at a high enough frame rate for certain clinical applications of fast motion such as capturing ultrasound images of the beating heart).

At least some of the systems, methods, apparatus, and/or code instructions described herein improve an underling technical process within the technical field of ultrasound imaging.

Accordingly, the systems and/or methods described herein are inextricably tied to computer technology and clinical imaging technology, in particular, to one or more physical ultrasound transducers for physically imaging a patient, to overcome an actual technical problem arising in clinical ultrasound imaging of rapidly moving tissue of a patient. Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the terms MLT-MLA and MLA-MLT are interchangeable.

Figure 2:
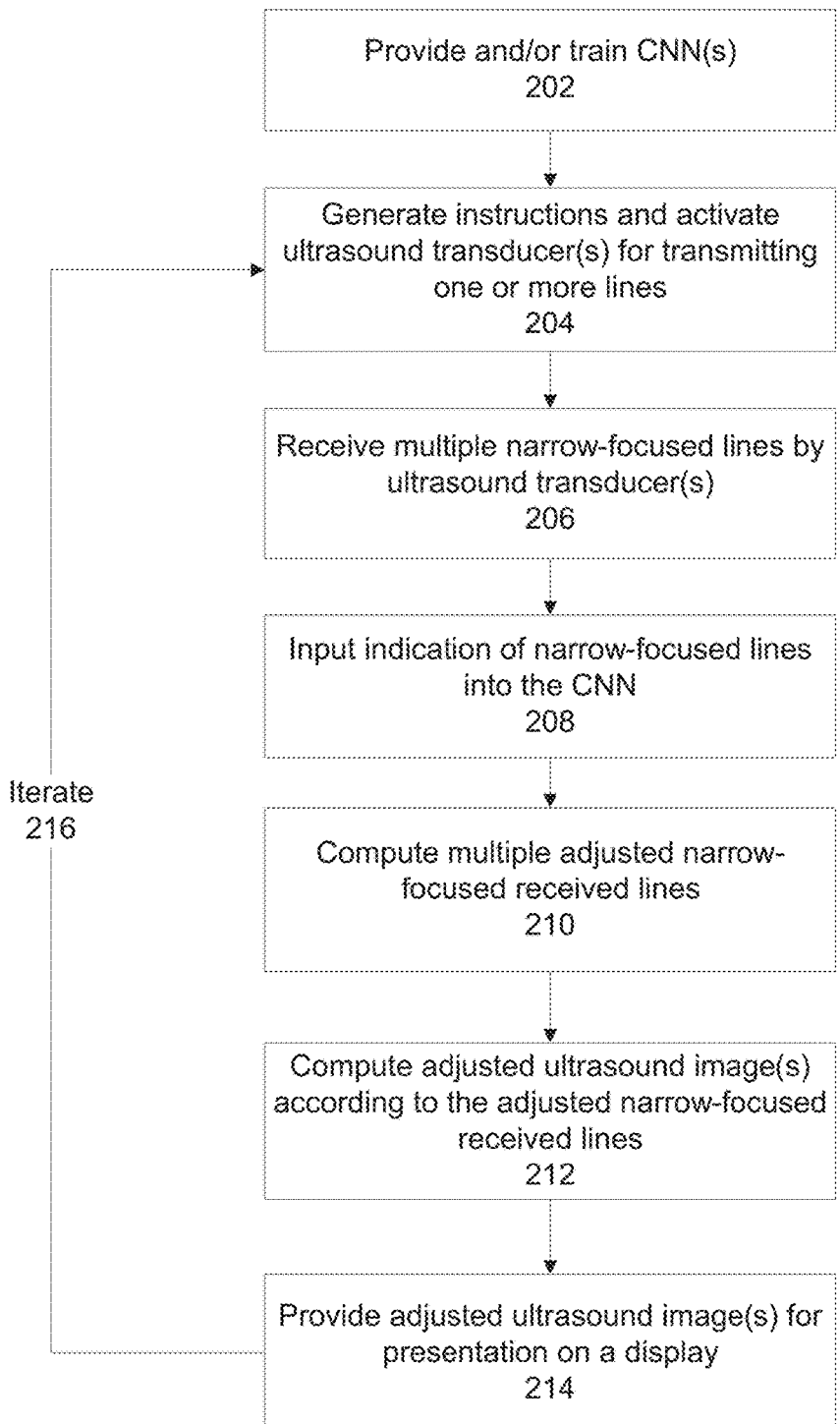
FIG. 2 is a flowchart of a method for imaging rapid motion of a target tissue(s) of a target patient, in accordance with some embodiments of the present invention.
Figure 3:
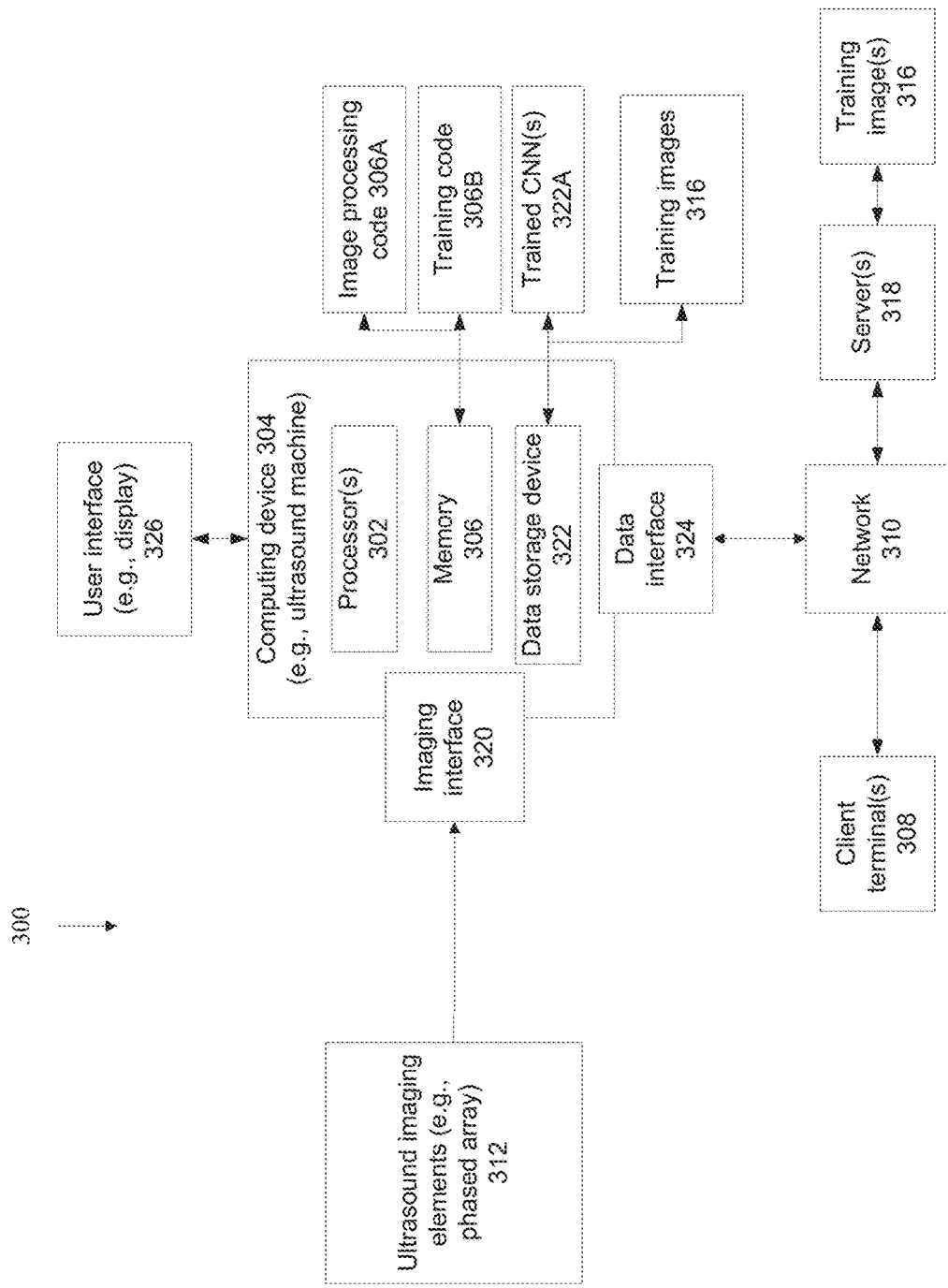
FIG. 3 is a block diagram of components of a system for correction of ultrasound imaging data acquired based on MLA and/or MLT processes and/or for training a CNN for computing the corrected ultrasound imaging data, in accordance with some embodiments of the present invention.
Figure 4:
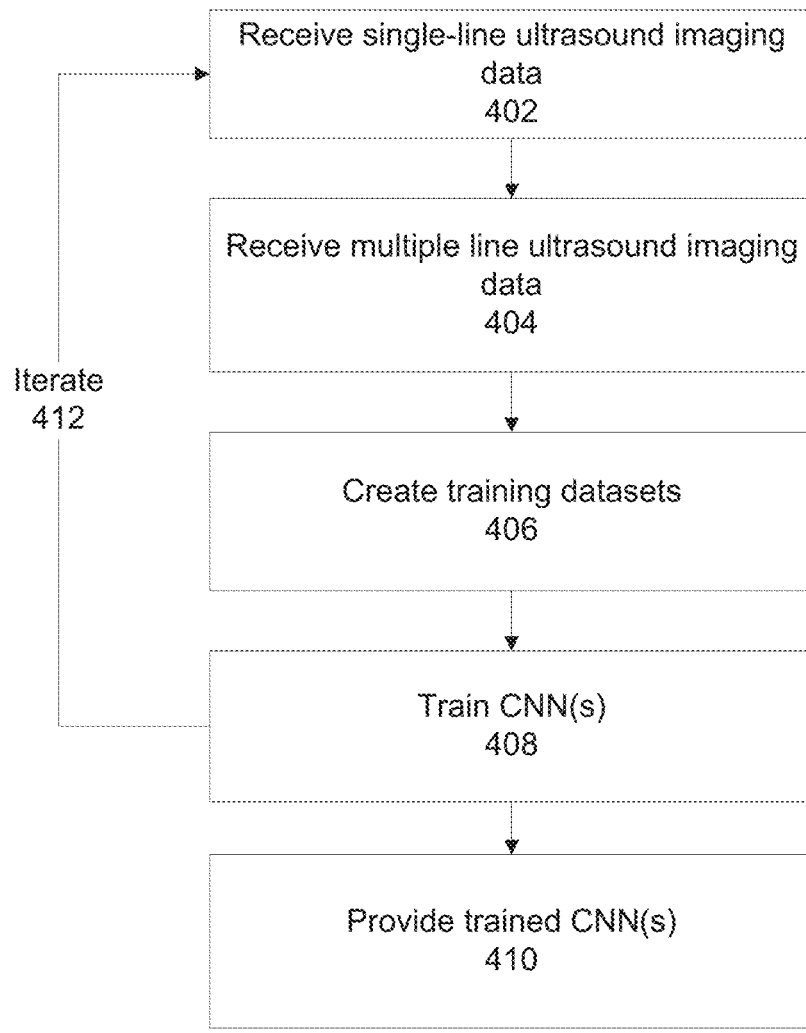
FIG. 4 is a flowchart of a method of training a CNN for outputting adjusted received lines for computing an adjusted ultrasound image for imaging rapid motion of a target tissue in a target patient, in accordance with some embodiments of the present invention.

Reference is now made to FIG. 2, which is a flowchart of a method for imaging rapid motion of a target tissue(s) of a target patient, in accordance with some embodiments of the present invention. Reference is also made to FIG. 3, which is a block diagram of components of a system 300 for correction of ultrasound imaging data acquired based on MLA and/or MLT processes and/or for training a CNN for computing the corrected ultrasound imaging data, in accordance with some embodiments of the present invention. Reference is also made to FIG. 4, which is a flowchart of a method of training a CNN for outputting adjusted received lines for computing an adjusted ultrasound image for imaging rapid motion of a target tissue in a target patient, in accordance with some embodiments of the present invention. System 300 may implement the acts of the method described with reference to FIG. 2 and/or FIG. 4, optionally by a hardware processor(s) 302 of a computing device 304 executing code instructions stored in a memory 306.

Optionally, computing device 304 is integrated with ultrasound imaging elements 312 into an ultrasound machine. For example, computing device 304 is implemented as a hardware device (e.g., chip, circuit, card) installed within a chassis of an ultrasound machine, as code stored on a memory of an ultrasound machine, and/or as an external component in communication with an ultrasound machine. Computing device 304 is arranged to be in electrical communication with ultrasound imaging elements 312, for receiving in real time, the imaging data (optionally raw) outputted by the ultrasound imaging elements 312 transmitting and receiving signals. Computing device 302 is installed to receive the imaging data outputted by ultrasound imaging elements 312 with minimal delay for real time correction of the imaging data for real time reconstructions of the ultrasound images. Alternatively, in some implementations, computing device 304 is located externally to ultrasound imaging elements 312, for example, when a delay is tolerated and/or when communication is fast enough to make the transmission delay insignificant. In such scenarios, computing device 304 may be implemented as, for example, a client terminal, a server, a virtual machine, a virtual server, a computing cloud, a mobile device, a hardware accelerator device, and/or a desktop device.

In implementations in which computing device 304 performs training of the CNN, computing device 304 and/or features of computing device 304 used for the training of the CNN may be implemented as a standalone device. Computing device 304 may be implemented as for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing device 204 may include locally stored software (e.g., training code 306B) that performs one or more of the acts described with reference to FIG. 4 for training the CNN. Computing device 204 may act as a server (e.g., network server, web server, a computing cloud, virtual server) and/or provide the trained CNN to a network connected server 218, which provides the trained CNN to client ultrasound machines for local installation and/or upgrade of locally installed trained CNNs, for locally correcting the imaging data for generation of ultrasound images.

Training of the CNN, and the application of the trained CNN to imaging data outputted by ultrasound imaging elements of different ultrasound machines, may be implemented by different computing devices 204, for example, one computing device 204 acts as a server for training the CNN, and transmitting the trained CNN to another computing device 204 installed within an ultrasound machine. In another implementation, the same computing device 204 performs the training of the CNN and uses the CNN to correct imaging data outputted by the ultrasound imaging elements 312.

Ultrasound imaging elements 312 are designed to generate one or more transmitted lines, and receive multiple lines in response. Ultrasound imaging elements 312 are designed to operate in MLA and/or MLT mode. Ultrasound imaging elements 312 may include a phased array, for dynamically steering the transmitted lines and/or for simultaneous transmission of multiple lines angled relative to each other. For training the CNN, ultrasound imaging elements 312 are designed to generate and transmit single lines, and receive single lines in response, for reconstructions of ultrasound images according to SLA and/or SLT. It is noted that ultrasound imaging elements 312 for training (i.e., in SLA and/or SLT mode) may be different, or the same, as ultrasound imaging elements 312 operating in MLA and/or MLT mode which use the trained CNN to generate corrected US images.

Computing device 304 receives imaging data (e.g., I/Q imaging data) outputted by ultrasound imaging elements 312, optionally via an imaging interface 320, for example, a local bus, a cable, a virtual interface, a physical interface, and a network connection.

Training images 316 reconstructed from imaging data of ultrasound imaging elements may be stored in a data storage device 322 of computing device 304, and/or stored on another device, for example, server 318 which may perform training of the CNN.

Hardware processor(s) 302 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 302 may include one or more processors (homogenous or heterogeneous), which may be arranged for parallel processing, as clusters and/or as one or more multi core processing units.

Memory 306 (also referred to herein as a program store, and/or data storage device) stores code instruction for execution by hardware processor(s) 302, for example, a random access memory (RAM), read-only memory (ROM), and/or a storage device, for example, non-volatile memory, magnetic media, semiconductor memory devices, hard drive, removable storage, and optical media (e.g., DVD, CD-ROM). When computing device 304 performs training of the CNN according to features described with reference to FIG. 4, memory 306 stores training code for training the CNN 306B. When computing device 304 performs correction of the imaging data according to features described with reference to FIG. 2, memory 306 stores imaging processing code 306A for executing the trained CNN.

Computing device 304 may include data storage device 322 for storing data. Data storage device 322 may be implemented as, for example, a memory, a local hard-drive, a removable storage device, an optical disk, a storage device, and/or as a remote server and/or computing cloud (e.g., accessed over network 310). When computing device 304 performs training of the CNN according to features described with reference to FIG. 4, data storage device 322 may store training images 316 and/or the trained CNN(s) 322A. When computing device 304 performs correction of the imaging data according to features described with reference to FIG. 2, data storage device 322 may store the trained CNN(s) 322A. It is noted that trained CNN 322A, and/or training images 316 may be stored in data storage device 322, with executing portions loaded into memory 306 for execution by processor(s) 302.

Computing device 304 may include data interface 324, optionally a network interface, for connecting to network 310, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 304 may access one or more remote servers 318 using network 310, for example, to download updated training images 316 and/or to download an updated version of image processing code 306A, training code 306B, and/or the trained CNN 322A.

Computing device 304 may communicate using network 310 (or another communication channel, such as through a direct link (e.g., cable, wireless) and/or indirect link (e.g., via an intermediary computing device such as a server, and/or via a storage device) with one or more of:

Client terminal(s) 308, which may be implemented as client ultrasound machines. For example, when computing device 304 trains the CNN, the trained CNN is provided to the client ultrasound machines for local correction of imaging data.

Server 318, for example, a PACS server for storing the reconstructed images, a server for generating the reconstructed images from the corrected imaging data, and a server training the CNN according to training images, and/or a server storing the trained CNN.

Computing device 304 includes or is in communication with a user interface 326 that includes a mechanism designed for a user to enter data (e.g., patient data) and/or view the ultrasound images reconstructed from the imaging data corrected by the trained CNN described herein. Exemplary user interfaces 226 include, for example, one or more of, a touchscreen, a display, a keyboard, a mouse, and voice activated software using speakers and microphone.

Referring now to FIG. 2, at 202, the CNN(s) is provided and/or trained. An exemplary method of training the CNN(s)

is described with reference to FIG. 4. Additional details of training the CNN(s) are described in the Examples section below.

Multiple CNNs may be trained. Each CNN may be trained according to a type of target tissue, which may be rapidly moving tissues, slow moving tissues, or tissues without significant motion (also referred to herein as static tissues). Exemplary target tissues include: heart, blood vessels, abdominal tissues (e.g., liver, pancreas, gall bladder), brain, a fetus, uterine tissues, pelvic tissues, and/or urinary system tissues (e.g., kidney, bladder, urinary ducts). Each CNN may be trained according to a set-up, including MLA, MLT, and combined MLT-MLA. Each CNN may be trained according to a MLA and/or MLT factor, for example, 2, 3, 4, 5, 6, 7, or higher numbers.

The CNN may be selected from multiple available CNNs. The selection may be performed manually by the user (e.g., via a user interface, for example, displaying a menu and/or icons of available CNNs, and/or available indications of CNNs according to imaging type). The selection may be performed manually by code that automatically determines the target tissue(s), for example, based on an analysis of the image itself, and/or analysis of data associated with the ultrasound imaging session (e.g., obtained from the electronic medical record of the patient, and/or according to a physical order for the ultrasound imaging, such as a clinical indication and/or target tissue imaging).

The CNN is trained on a training set that includes pairs of ultrasound imaging data capturing the target tissue (optionally during rapid motion of the target tissue) of sample patients. Each of the pairs of ultrasound imaging data of the training set includes a single-line ultrasound imaging data captured based on ultrasound transducer(s) receiving a single line in response to a transmitted single narrow-focused pulse (e.g., based on SLT and SLA), and a multiple-line ultrasound imaging data captured based on ultrasound transducer(s) receiving multiple narrow-focused lines in response to simultaneously transmitted line(s) with pre-defined focus width (e.g., based on MLT, MLA, or MLT-MLA). The CNN is trained for outputting adjusted narrow-focused received lines according to an input of narrow-focused received lines.

Figure 5:
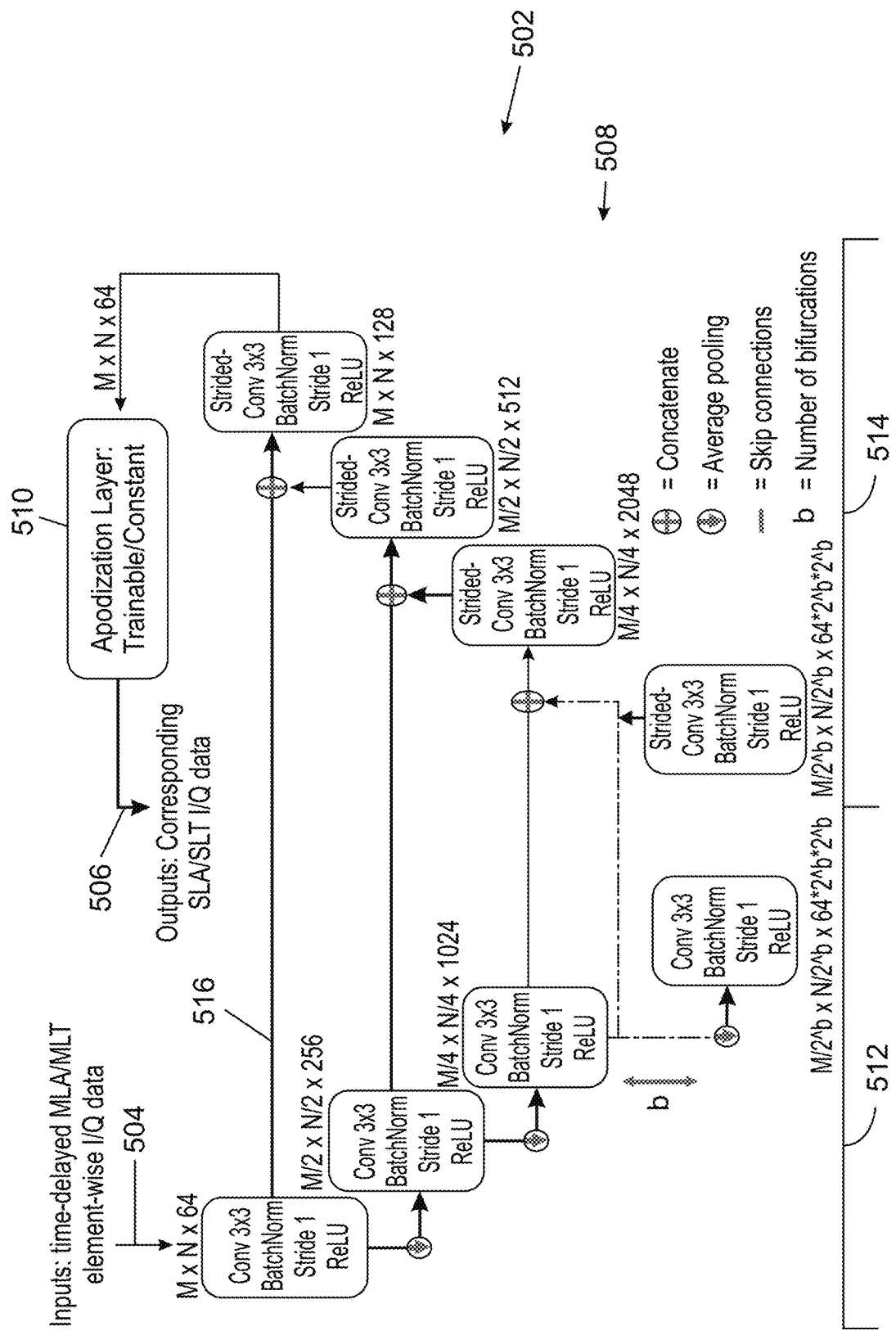
FIG. 5 is a block diagram of an exemplary architecture of a CNN that outputs computed adjusted narrow-focused receive lines according to an input of an indication of narrow-focused received lines received by an ultrasound transducer(s), in accordance with some embodiments of the present invention.

Reference is now made to FIG. 5, which is a block diagram of an exemplary architecture of a CNN 502 that outputs computed adjusted narrow-focused receive lines 504 according to an input of an indication of narrow-focused received lines 506 received by an ultrasound transducer(s), in accordance with some embodiments of the present invention.

Input 504 may include time-delayed, element-wise (e.g., per ultrasound transducer element of a phased array) I/Q imaging data, received when an MLT, MLA and/or MLT-MLA set-up is used for ultrasound imaging. Input 504 may be obtained from the ultrasound transducer(s) that include ultrasound elements arranged as a phased array. The input 504 including the indications of the narrow-focused received lines are inputted into a first layer of the interpolation layers 508 of the CNN 502 as raw I/Q output of each of elements of the ultrasound transducer(s).

Output 506 of CNN 502 may include the corresponding I/Q imaging, corrected to correlate to imaging data that would otherwise be obtained by an SLA and/or SLT set-up (i.e., where in fact, such SLA and/or SLT set-up is not used, but rather the MLT, MLA and/or MLT-MLA set-up is used).

CNN 502 includes multiples interpolation layers 508 followed by an apodization layer 510. Interpolation layers 508 are arranged as a downsampling track 512 followed by an upsampling track 514. Interpolation layers 508 of downsampling track 512 include average pooling layers, for example, implemented as respective convolutional layers (e.g., 3X), a BatchNorm Stride 1 layer, and a ReLu layer. Sizes of features (e.g., images) extracted by each interpolation layers 508 of downsampling track 512 are successively reduced by half. Interpolation layers 508 of upsampling track 514 include respective strided convolutional layers (e.g., 3X), and optionally, a BatchNorm Stride 1 layer, and a ReLu layer. Sizes of features (e.g., images) inputted into each successive interpolation layers 508 of downsampling track 512 are increased by a factor of two.

Respective skip connections (one skip connection marked for clarity as 516) connect each interpolation layers of the downsampling track 512 to a corresponding interpolayer layer of the upsampling track 514.

It is to be understood that the architecture described with reference to FIG. 5 is exemplary only. While the network architecture described with reference to FIG. 5 includes a downsampling track followed by an upsampling track as demonstrated, the architecture is not necessarily limited to the specific architecture shown in FIG. 5. Other regression network architectures that are suitable for the described task may be implemented.

Optionally, apodization layer 510 includes a convolutional layer. Optionally, the convolutional layer receives input from each of multiple channels corresponding to each of the elements of the ultrasound transducer(s) (e.g., each element of the phased array). Optionally, the convolutional layer of the apodization layer performs point-wise convolutions (i.e., 1×1) for each element's channel in the CNN, and the results are added to the weights of the convolution. The weights of the channel may be learned, and/or fixed with an apodization window, for example, a Hann window, or other constant apodization window.

Referring now back to FIG. 2, at 204, instructions for activating the ultrasound transducer(s) for simultaneously transmitting one or more lines with a predefined focus width, are generated. A single line may be generated when using MLT set-up. Multiple lines may be generated when using MLA, and/or MLT-MLA set-up. The ultrasound transducer(s) is activated according to the instructions, for generating the one or more single lines.

Optionally, when SLT-MLA set-up is implemented, a single wide-focus line with predefined focus width is transmitted.

Alternatively, when MLT-SLA set-up is implemented, multiple narrow-focused lines are transmitted.

Alternatively, when MLT-MLA set-up is implemented, multiple wide-focused lines are transmitted.

At 206, multiple narrow-focused received lines are received by the ultrasound transducer(s) in response to the transmitted line(s). The lines are received after being reflected at least by the target tissue(s). An indication of the multiple narrow-focused received lines is outputted by the ultrasound transducer(s).

Optionally, each of multiple elements of the ultrasound transducer (e.g., arranged as a phased array) outputs respective imaging data. The indication of the multiple narrow-focused received lines is provided according to the imaging data from the multiple elements.

Optionally, the indication of the narrow-focused received lines includes raw in-phase and quadrature (I/Q) output of each of the elements. Alternatively or additionally, the data outputted by the elements in a radiofrequency (RF) format and converted to the I/Q domain. Optionally, an odd number of lines are received for each transmitted line (e.g., a single line for MLA, or multiple transmitted lines for MLT-MLA). The odd number is a factor for the increase in the frame rate of the adjusted ultrasound images. Alternatively, an even number of lines are received for each transmitted line.

At 208, the indication of the narrow-focused received lines is inputted into the CNN. The indication of the narrow-focused received lines may be inputted into the CNN in real time, and dynamically, as the ultrasound transducer is being manipulated by the user performing the ultrasound imaging session.

At 210, the CNN computes an indication of multiple adjusted narrow-focused received lines according to the inputted indication of the narrow-focused received lines.

Optionally, the adjusted narrow-focused received lines outputted by the CNN include adjusted I/Q outputs for input into a process that generates ultrasound images based on I/Q outputs of elements.

At 212, an adjusted ultrasound image(s) is computed according to the adjusted narrow-focused received lines. The adjusted ultrasound image may be computed based on the adjusted I/Q outputs of the CNN, by the process that generates ultrasound images based on I/Q outputs of ultrasound transducer elements.

At 214, the adjusted ultrasound image is provided for presentation on a display. The adjusted ultrasound image may be stored, for example, locally, by a PACS server, for example, as part of the electronic medical record of the patient.

Figure 6:
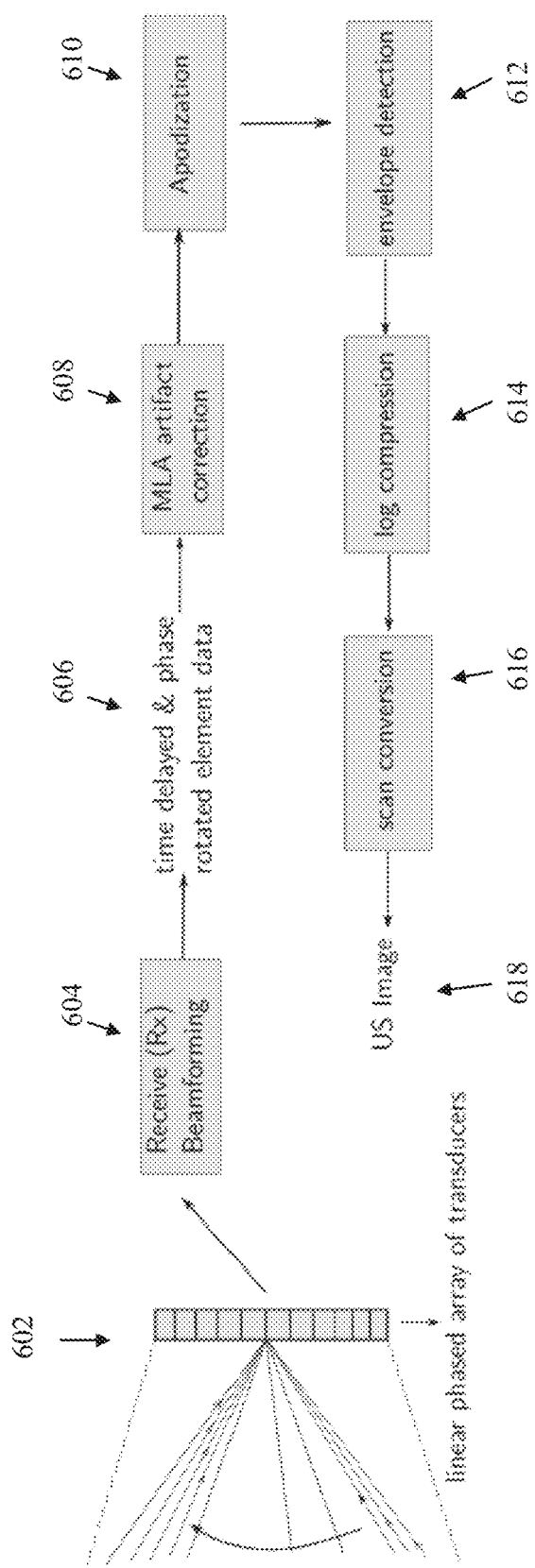
FIG. 6 is a schematic depicting an exemplary dataflow for computing an ultrasound image based on an indication of multiple adjusted narrow-focused received lines computed by a trained CNN according to the inputted indication of the narrow-focused received lines, as described herein.

Reference is now made to FIG. 6, which is a schematic depicting an exemplary dataflow for computing an ultrasound image based on an indication of multiple adjusted narrow-focused received lines computed by a trained CNN according to the inputted indication of the narrow-focused received lines, as described herein. At 602, elements (e.g., linear phased array) of ultrasound transducer(s) output an indication of received multiple narrow-focused lines, for example, as described with reference to act 206 of FIG. 2. The narrow-focused lines are received in response to one or more transmitted lines (depending on the set-up type being implemented), for example, as described with reference to act 204 of FIG. 2. At 606, time delayed and/or phase rotated element data is computed. At 608 and 610, the CNN described herein performs correction of the received narrow-focused lines to compute adjusted narrow-focused received lines, for example, as described with reference to act 208 and 210 of FIG. 2. The apodization of 610 may be performed by the apodization layer of the CNN, for example, as described herein with reference to FIG. 5. At 612, envelope detection is performed. At 614, log compression is performed, At 616, scan conversion is performed. At 618, the ultrasound image is computed for presentation on a display.

Referring now back to FIG. 2, At 216, one or more acts 204-214 are iterated. The iterations dynamically computes ultrasound images in real time, as the operator manipulates the ultrasound transducer to various orientations and/or positions on the body of the target individual. The real time dynamic iterations provide for real time dynamic imaging of rapidly moving target tissues and/or organs, for example, of the heart of the target individual.

Referring now to FIG. 4, at 402, an indication of single-line imaging data may be obtained by ultrasound imaging of the target tissue(s) of the sample individual, for example, based on standard SLT/SLA set-ups. A single line (e.g., single narrow-focused pulse) is transmitted and a single line is received in response to the transmitted single line, according to standard ultrasound imaging practice.

In another implementation, the single-line imaging data may be obtained by ultrasound imaging of a phantom and/or dummy that simulates real target tissue, rather than or in addition to obtaining ultrasound imaging data from a real individual.

At 404, an indication of multiple lines imaging data is obtained by ultrasound imaging of the target tissue(s) of the sample individual, for example, based on standard MLA and/or MLT and/or MLT-MLA set-ups.

Optionally, the ultrasound transducer(s) is activated for simultaneously transmitting one or more lines with a pre-defined focus width, and receiving an indication of multiple narrow-focused received lines in response to the transmitted line(s).

In another implementation, the multiple-line imaging data may be obtained by ultrasound imaging of a phantom and/or dummy that simulates real target tissue, rather than or in addition to obtaining ultrasound imaging data from a real individual.

Optionally, the indication of multiple lines is emulated from single-line imaging data, for example, when an ultrasound imaging device based on MLA and/or MLT and/or MLT-MLA is not available, but an ultrasound imaging device based on SLT/SLA is available. For example, the target tissue(s) of the patient are imaged using the ultrasound transducer via the SLT/SLA set-up. The MLA and/or MLT and/or MLT-MLA imaging data is emulated from the imaging data obtained via the SLT/SLA set-up. Optionally, the multi-line imaging data corresponding to the single-line imaging data is computed from the single-line imaging data by decimating the received pre-beamformed data (e.g., to emulate MLA imaging data). Alternatively or additionally, the multi-line imaging data corresponding to the single-line imaging data is computed from the single-line imaging data by summation of the received pre-beamformed data (e.g., to emulate MLT imaging data).

At 406, one or more training datasets are created. The training dataset includes pairs of ultrasound imaging data. Each pair includes the single-line ultrasound imaging data (e.g., obtained in 402) and the corresponding multiple-line ultrasound imaging data (e.g., obtained in 404).

Training dataset may be created according to the type of target tissue and/or body region that was imaged, for example, the heart, the kidney, the liver, static abdominal organs (e.g., liver, gallbladder, pancreas, kidney), urinary system (e.g., kidney, bladder).

At 408, one or more CNNs are trained according to the training dataset. Multiple CNNs may be trained, each for imaging a certain type of target tissue and/or body region, according to the corresponding training dataset.

The CNN(s) is trained for outputting adjusted narrow-focused received lines according to an input of the indication of narrow-focused received lines. Conceptually the CNN corrects imaging data obtained based on MLA and/or MLT and/or MLT-MLA set-up to correlate to imaging data obtained by SLA/SLT set-ups. The correction increases the quality of the reconstructed images and/or reduces artifacts in the reconstructed images, where the reconstructed image is closer (i.e., more correlated) to images obtained by SLA/SLT set-ups than to images obtained by the actual MLA and/or MLT and/or MLT-MLA set-ups.

The architecture of the CNN may be, for example, as described with reference to FIG. 5. The weights of the channel may be learned, and/or fixed with a Hann window.

Optionally, the CNN is trained by computing a discrepancy between the adjusted narrow-focused received lines computed by the CNN and the single-line imaging data denoting ground truth, and minimizing the discrepancy according to code for an optimizer. The discrepancy may computed, for example, according to L1 norm training loss.

At 410, the trained CNN(s) is provided. The trained CNN(s) may be locally stored by the computing device, and/or forwarded to the computing device, for example, where training is centrally performed by a server that transmits the trained CNN(s) to ultrasound imaging devices over a network and/or via a portable memory storage device.

At 412, the trained CNN(s) may be updated and/or re-trained according to new pairs of training ultrasound images, by iterating acts 402-408.

Additional details of training the CNN(s) are described in the Examples section below.

Various implementations of at least some of the systems and/or methods and/or code instructions stored in a data storage device executed by one or more processors delineated hereinabove and as claimed in the claims section below find experimental support in the following examples.

Examples

Reference is now made to the following examples, which together with the above descriptions illustrate some implementations of the systems and/or methods and/or code instructions stored in a data storage device executed by one or more processors described herein in a non-limiting fashion.

The results of the experiments provide evidence that at least some of the systems, apparatus, methods, and/or code instructions described herein provide significant improvement in the visual image quality of ultrasound images and/or in object measures such as contrast ratio (CR) and/or contrast-to-noise ratio (CNR) computed for the generated ultrasound images, while preserving resolution.

A first set of experiments was designed to evaluate training of the CNN described herein for processing imaging data acquired based on an MLA setup. Inventors generated a training dataset for training the CNN described herein using cardiac ultrasound imaging data from six patients. Each patient contributed 4-5 cine loops, where each cine loop includes 32 frames. The data was acquired using a General Electric (GE)™ experimental breadboard ultrasound system. The same transducer was used for both phantom and cardiac acquisition. Excitation sinusoidal pulses of 1.75 cycles, centered around 2.5 MegaHertz (MHz), were transmitted using 28 central elements out of the total 64 elements in the probe with a pitch of 0.3 millimeters (mm), elevation size of 13 mm and elevation focus of 100 mm. The depth focus was set at 71 mm. In order to assess the desired aperture for MLA setup, Field II simulator described with reference to Jensen, J. A.: *Field: A program for simulating ultrasound systems. In: 10$^{TH}$ Nordicbaltic Conference on Biomedical Imaging, VOL. 4, Supplement 1, Part* 1:351-353, Citeseer (1996) was used as described with reference to Rabinovich, A., Friedman, Z., Feuer, A.: *Multiline acquisition with minimum variance beamforming in medical ultrasound imaging. IEEE transactions on ultrasonics, ferroelectrics, and frequency control* 60(12) (2013) 2521-2531 using the transducer impulse response and tri-state transmission excitation sequence, requiring a minimal insonification of −3 decibels (dB) for all MLAs from a single Tx.

On the Rx side, the I/Q demodulated signals were dynamically focused using linear interpolation, with an f-number of 1. The FOV was covered with 140/140 Tx/Rx lines in SLA mode, 28/140 Tx/Rx lines in the 5-MLA mode, and 20/140 Tx/Rx lines in the 7-MLA mode. For both phantom and cardiac cases, the data were acquired in the SLA mode. 5-MLA and 7-MLA data was obtained by appropriately decimating the Rx pre-beamformed data.

In total, 745 frames from five patients were used for training and validation, while keeping the cine loops from the sixth patient for testing. The data set comprised pairs of beamformed I/Q images with Hann window apodization, and the corresponding 5-MLA and 7-MLA pre-apodization samples with the dimensions of 652×64×140 (depth×elements×Rx lines). The MLA data was acquired by decimation of the Tx lines of the SLA samples by the MLA factor (m=5, 7).

Dedicated CNNs were trained for the reconstruction of SLA images from 5-MLA and 7-MLA. Each CNN was trained to a maximum of 200 epochs on mini batches of size 4. The performance of the trained CNN was assessed using cine loops from one patient excluded from the training/validation set. From two cine loops, each containing 32 frames, pairs of 5-MLA and 7-MLA samples and their corresponding SLA images were generated, resulting in 64 test samples. For quantitative evaluation of the performance of the CNN, a decorrelation criterion (denoted Dc) that evaluates the artifact strength (e.g., as described with reference to Bjastad, T., Aase, S. A., Torp, H.: *The impact of aberration on high frame rate cardiac b-mode imaging. IEEE Transactions on Ultrasonics Ferroelectrics and Frequency Control* 54(1) (2007) 32) was computed, and the SSIM (structural similarity index) criterion with respect to the SLA image was computed (e.g., as described with reference to Wang, Z., Bovik, A. C., Sheikh, H. R., Simoncelli, E. P.: *Image quality assessment: from error visibility to structural similarity. IEEE transactions on image processing* 13(4) (2004) 600-612). In addition, the performance of the trained CNN was tested on four frames acquired from the GAMMEX Ultrasound 403GS LE Grey Scale Precision Phantom.

Quantitative results for image results by the trained CNN for the cardiac test set are summarized in Table 1 below. Table 1 presents a comparison of average decorrelation and SSIM measures between the original and corrected 5-MLA and 7-MLA cardiac images.

TABLE 1

|  | SLA | 5-MLA | | 7-MLA | |
| --- | --- | --- | --- | --- | --- |
|  | Original | Original | Corrected | Original | Corrected |
| Decorrelation | 0.03/−0.04 | 22.03 | 0.69 | 31.7 | 0.827 |
| SSIM | — | 0.75 | 0.876 | 0.693 | 0.826 |

The results presented in Table 1 illustrate a major significant improvement in decorrelation and SSIM for both images acquired using 5-MLA and 7-MLA. The correlation coefficient profile of the corrected 5-MLA and 7-MLA approaches that of the SLA. Moreover, the corrected 7-MLA (corrected by the CNN as described herein) performance approaches that of 5-MLA, suggesting the feasibility of larger MLA factors.

Figure 7:
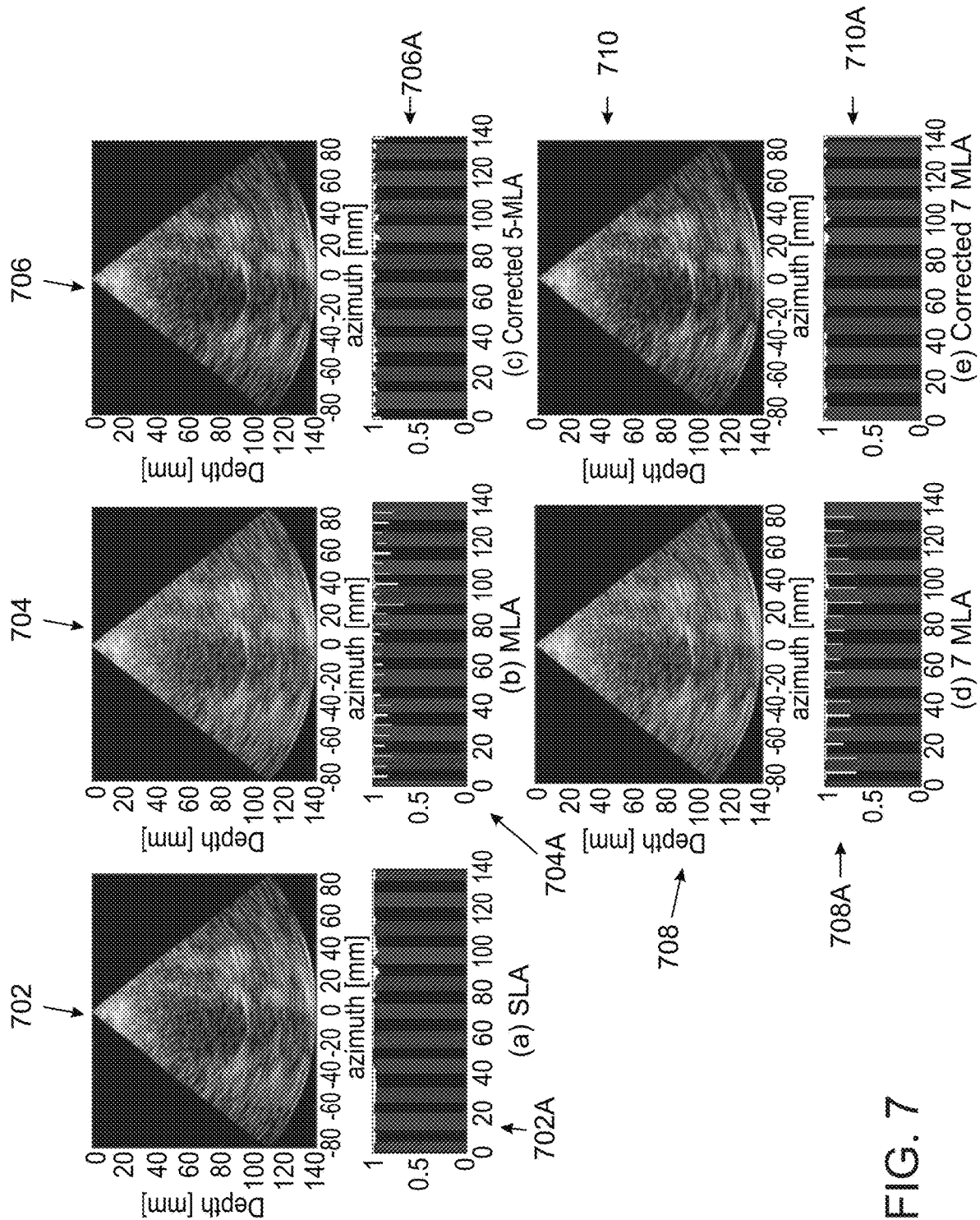
FIG. 7 is a which includes examples of test images from cardiac sequences for the experiment described herein, created based on SLA, 5-MLA, corrected 5-MLA, 7-MLA, and corrected 7-MLA, in accordance with some embodiments of the present invention.

Reference is now made to FIG. 7, which includes examples of test images from cardiac sequences, created based on SLA 702, 5-MLA 704, corrected 5-MLA 706, 7-MLA 708, and corrected 7-MLA 710, in accordance with some embodiments of the present invention. Corrected 5-MLA 706 and corrected 7-MLA 710 were generated based on output of the trained CNN. Each image 702-710 is depicted along with a corresponding plot 702A-710A of the correlation coefficients between adjacent lines.

Table 2 presents quantitative image reconstruction results for the phantom test set. Table 2 presents a comparison of average decorrelation and SSIM measures between original and corrected 5-MLA and 7-MLA phantom images.

TABLE 2

|  | SLA | 5-MLA | | 7-MLA | |
| --- | --- | --- | --- | --- | --- |
|  | Original | Original | Corrected | Original | Corrected |
| Decorrelation | 0.06/−0.089 | 19.53 | 0.457 | 32.34 | 0.956 |
| SSIM | — | 0.815 | 0.96 | 0.793 | 0.935 |

The results summarized in Table 2 show a significant improvement in the image quality for both 5-MLA and 7-MLA. The results shown in Table 2 suggest that the CNN trained on real cardiac data generalize well to the phantom data without any further training or fine-tuning. For comparison, Bjastad, T., Aase, S. A., Torp, H.: *The impact of aberration on high frame rate cardiac b-mode imaging. IEEE Transactions on Ultrasonics Ferroelectrics and Frequency Control* 54(1) (2007) 32 reported a decorrelation value of −1.5 for a phantom image acquired in a 4-MLA mode with STB compensation, while in contrast processing by the trained CNN described herein provides closer to zero Dc values, 0.457 for 5-MLA and 0.956 for 7-MLA, which both use a greater decimation rate. The slight dissimilarities in the recovered data may be explained by the acquisition method being used. Since the scanned object was undergoing motion, there is a difference between all but a central line in each MLA group and the matching lines in SLA. It is hypothesized by inventors that training the CNN on images of static organs may further improve performance. Independently, small areas with vertical stripes were observed in several images. The origin of the stripes may be a coherent summation of the beamformed lines across the moving object. Since the frame rate of the employed acquisition sequence was slower than of genuine MLA acquisition, the magnitude of the artifact is probably exaggerated.

A second set of experiments was designed to evaluate training of the CNN described herein for processing imaging data acquired based on an MLT setup. Acquisition of real MLT data is a complicated task that requires a highly flexible ultrasound system. Such ultrasound system for acquiring MLT data was not available. Instead, Inventors simulated imaging data acquired based on the MLT setup using the data acquired in SLT mode, by summation of the received data prior to the beamforming stage, as described in additional detail with reference to Prieur, F., Denarie, B., Austeng, A., Torp, H.: *Correspondence-multi-line transmission in medical imaging using the second-harmonic signal. IEEE trans. on ultrasonics, ferroelectrics, and frequency control* 60(12), 2682-2692 (2013), and Rabinovich, A., Feuer, A., Friedman, Z.: *Multi-line transmission combined with minimum variance beamforming in medical ultrasound imaging. IEEE trans. On ultrasonics, ferroelectrics, and frequency control* 62(5), 814-827 (2015) for the fundamental and tissue harmonic modes. It should be noted that while the MLT setup may be simulated almost accurately in a fundamental harmonic case, there is a restriction in the tissue harmonic mode due to the nonlinearity of its forward model. As described with reference to Prieur, F., Denarie, B., Austeng, A., Torp, H.: *Correspondence-multi-line transmission in medical imaging using the second-harmonic signal. IEEE trans. on ultrasonics, ferroelectrics, and frequency control* 60(12), 2682-2692 (2013), in the tissue harmonic mode, the summation of the data sequentially transmitted in two directions provides a good enough approximation for the simultaneous transmission in the same directions if the MLT separation angle is above 15 degrees. The assumption behind the second set of experiments is that this approximation holds for a higher MLT number, as long as the separation angle remains the same, since the beam profile between two beams is mainly affected by those beams. For this reason, 4-MLT and 6-MLT with separation angles of 22.6 degrees and 15.06 degrees, respectively, were selected for the second set of experiments.

For the second set of experiment, imaging of quasi-static internal organs, such as bladder, prostate, and various abdominal structures, was selected. Such quasi-static internal organs were selected since the simulated MLT of the rapidly moving organ may alter the cross-talk artifact. The second experiment was performed with the data acquired using a GE ultrasound system, scanning 6 healthy human volunteers and a tissue mimicking phantom (GAMMEX Ultrasound 403GS LE Grey Scale Precision Phantom). The tissue harmonic mode was selected for the second experiment, being a common mode for cardiac imaging, with a contrast resolution that is superior to the fundamental harmonic, at either $f_0$ or $2f_0$. The ultrasound scans were performed in a transversal plane by moving a probe in a slow longitudinal motion in order to reduce the correlation in the training data acquired from the same patient. The acquisition frame rate was 18 frames per second. Excitation sinusoidal pulses of 2.56 cycles, centered around $f_0$=1.6 MegaHertz (MHz), were transmitted using a 64-element phased array probe with the pitch of 0.3 millimeters (mm). No apodization was used on transmit. On receive, the tissue harmonic signal was demodulated (I/Q at 3.44 MHz and filtered. A 90.3 degree field-of-view (FOV) was covered with 180 beams. In the case of MLT, the signals were summed element-wise with the appropriate separation angles.

Afterward, both SLT and MLT were dynamically focused and summed. In the simulated MLT mode the data were summed after applying a constant apodization window (Tukey, $\alpha$=0:5) as the best apodization window, as described with reference to Tong, L., Gao, H., D'hooge, J.: *Multi-transmit beam forming for fast cardiac imaging-a simulation study. IEEE trans. on ultrasonics, ferroelectrics, and frequency control* 60(8), 1719-1731 (2013), and Tong, L., Ramalli, A., Jasaityte, R., Tortoli, P., D'hooge, J.: *Multi-transmit beam forming for fast cardiac imaging experimental validation and in vivo application. IEEE transactions on medical imaging* 33(6), 1205-1219 (2014). At training, non-apodized MLT and SLT data were presented to the CNN as the input and the desired output, respectively.

The CNN was trained using SLT I/Q image data to generate both simulated MLT input data as well as the corresponding SLT (i.e., artifact-free) reference output. The CNN was trained as a regressor minimizing the $L_1$ discrepancy between the predicted CNN outputs and the corresponding ground-truth SLT data. The loss was minimized using Adam optimizer (e.g., as described with reference to Kingma, D. P., Ba, J.: *Adam: A method for stochastic optimization. ICLR* (2015), with the learning rate set to $10^{-4}$. A total of 750 frames from the acquired sequences were used for training. The input to the CNN was a MLT I/Q image of size 696×180×64 (depth×lines×elements) and the output was an SLT-like I/Q image data of size 696×180 (depth× lines). The training was performed separately for the I and Q components of the image.

In order to evaluate the performance of the CNNs trained on 4- and 6-MLT setups, a test set was created. The test set included two frames from the bladder and one frame from a different anatomy acquired from a patient excluded from the training set, and a phantom frame. All the selected test frames were unseen during training. The latter two frames portray different image classes that were not part of the training set. Evaluation was conducted both visually and quantitatively using CR and CNR objective measures defined as follows:

$$CR = 20\log_{10}\left(\frac{\mu_{lesion}}{\mu_{background}}\right)$$

$$CR = \frac{|\mu_{background} - \mu_{lesion}|}{\sqrt{\sigma^2_{background} + \sigma^2_{lesion}}}$$

where:
μ denotes the mean of the uncompressed envelope, and
σ denotes the standard deviation.

Figure 8:
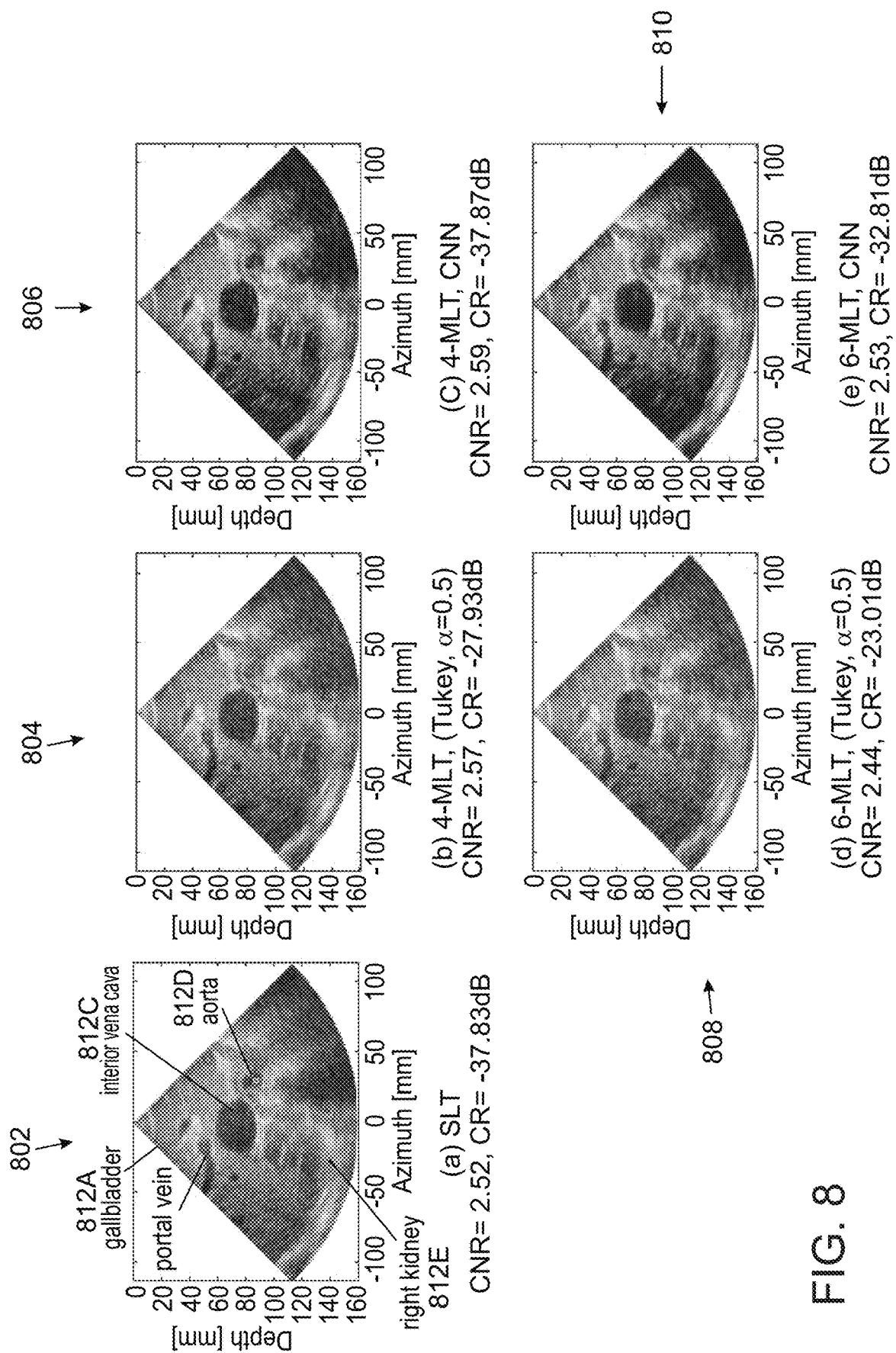
FIG. 8 is an example of a SLT groundtruth image, and artifact-corrected 4-MLT image and 6-MLT images computed by the CNN trained as part of the second set of experiments, in accordance with some embodiments of the present invention.

Reference is now made to FIG. 8, which is a schematic depicting an example of a SLT groundtruth image 802, and artifact-corrected 4-MLT image 804 806 and 6-MLT images 808 810 computed by the CNN trained as part of the second set of experiments, in accordance with some embodiments of the present invention. SLT groundtruth image 802 demonstrates a number of anatomical structures in abdominal area, as depicted by call out numbers 812A-E (i.e., Gallbladder, portal vein, inferior vena cava, aorta, and right kidney). As shown by computed images 806 and 810, the trained CNN processing has restored the CR loss caused by the MLT cross-talk artifact for the 4-MLT, and improved the CR by 9.8 dB for the 6-MLT, as measured for example, for regions of images 806 and 810 corresponding to aorta 812D and to a background region 812F of ground truth 802. Images 806 and 810 which were reconstructed based on output of the CNN are compared to corresponding MLT images 804 and 808, reconstructed with Tukey (α=0:5) window apodization on receive, a common method to the attenuation of the receive cross-talk artifact. As is visually apparent, images 806 and 810 reconstructed based on output of the CNN are very similar to ground truth SLT image 802 in comparison to images 804 and 808 reconstructed using other standard methods, which are of lower quality and/or include artifacts.

The CNR and CR results are summarized in the Table below:

| Image | Reference in FIG. 8 | CNR | CR (dB) |
| --- | --- | --- | --- |
| SLT (groundtruth) | 802 | 2.52 | −37.33 |
| 4-MLT computed based on CNN | 806 | 2.59 | −37.87 |
| 4-MLT (standard method) | 804 | 2.57 | −27.93 |
| 6-MLT computed based on CNN | 810 | 2.53 | −32.81 |
| 6-MLT (standard method) | 808 | 2.44 | −23.01 |

A slight CNR improvement as compared to the apodized MLT was measured in all cases, except for the 6-MLT for the tissue mimicking phantom, where the CNR remained the same. The performance of the CNN described herein, verified on the testing set frames of internal organs, and of a tissue mimicking phantom, suggests that the CNN generalizes well to other scenes and patients, despite being trained on a small dataset of bladder frames.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant ultrasound set-ups will be developed and the scope of the terms SLT, SLA, MLT, MLA, and MLT-MLA are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. An ultrasound device for imaging rapid motion of a certain tissue in a target patient, comprising:
   at least one ultrasound transducer;
   a memory storing code;
   at least one hardware processor coupled to the at least one ultrasound transducer and the memory for executing the stored code, the code comprising:
      code for activating the at least one ultrasound transducer for simultaneously transmitting at least one line with a predefined focus width, and receiving from the at least one ultrasound transducer an indication of a plurality of narrow-focused received lines in response to the transmitted at least one line,
      code for inputting the indication of the plurality of narrow-focused received lines into a convolutional neural network (CNN), wherein the CNN is trained on a training set comprising a plurality of pairs of ultrasound imaging data capturing rapid motion of the certain tissue of at least one sample patient, wherein each pair of the plurality of pairs of ultrasound imaging data includes a single-line ultrasound imaging data captured based on at least one ultrasound transducer receiving a single line in response to a transmitted single narrow-focused pulse, and a multiple-line ultrasound imaging data captured based on at least one ultrasound transducer receiving a plurality of narrow-focused lines in response to simultaneously transmitted at least one line with predefined focus width, and outputting by the CNN, a plurality of adjusted narrow-focused received lines,
      code for computing an adjusted ultrasound image according to the plurality of adjusted narrow-focused received lines, and
      code for outputting the adjusted ultrasound image for presentation on a display.

2. The ultrasound device of claim 1, wherein the simultaneously transmitted at least one line with predefined focus width is a single wide-focus line.

3. The ultrasound device of claim 2, wherein the plurality of received lines received in response to the single wide-focused line are an odd number for increasing the frame rate of the adjusted ultrasound images by the odd number.

4. The ultrasound device of claim 1, wherein the simultaneously transmitted at least one line with predefined focus width comprises a plurality of narrow-focused lines.

5. The ultrasound device of claim 1, wherein the simultaneously transmitted at least one line with predefined focus width comprises a plurality of wide-focused lines.

6. The ultrasound device of claim 1, wherein the at least one ultrasound transducer comprises a plurality of elements arranged as a phased array, wherein the indication of the plurality of narrow-focused received lines inputted into the CNN comprises raw in-phase and quadrature (I/Q) output of each of the plurality of elements, and the plurality of adjusted narrow-focused received lines outputted by the CNN comprise adjusted I/Q outputs for input into a process that generates ultrasound images based on I/Q outputs of elements.

7. The ultrasound device of claim 1, wherein the CNN comprises a plurality of interpolation layers followed by an apodization layer.

8. The ultrasound device of claim 7, wherein the plurality of interpolation layers comprise a plurality of convolutional layers arranged as a downsampling track followed by an upsampling track, wherein a plurality of skip connections connect each interpolation layer of the downsampling track to a corresponding interpolayer layer of the upsampling track.

9. The ultrasound device of claim 8, wherein the downsampling track comprises a plurality of average pooling layers and the upsampling track comprises a plurality of strided convolutions.

10. The ultrasound device of claim 7, wherein the at least one ultrasound transducer comprises a plurality of elements arranged as a phased array, wherein the indication of the plurality of narrow-focused received lines inputted into a first layer of the plurality of interpolation layers of the CNN comprises raw I/Q output of each of the plurality of elements.

11. The ultrasound device of claim 7, wherein the at least one ultrasound transducer comprises a plurality of elements arranged as a phased array, wherein the apodization layer comprising a convolutional layer for each of a plurality of channels corresponding to each of the plurality of elements, and wherein computed point-wise convolutions are added to the weights of the convolution.

12. The ultrasound device of claim 1, wherein the at least one ultrasound transmitter transmits a plurality of lines, wherein each lines of the plurality of transmitted lines comprise a respective single wide-focused line.

13. A system for training a CNN of an ultrasound device for imaging rapid motion of a certain tissue in a target patient, comprising:

at least one ultrasound transducer;
a memory storing code;
at least one hardware processor coupled to the at least one ultrasound transducer and the memory for executing the stored code, the code comprising:
code for activating the at least one ultrasound transducer for simultaneously transmitting at least one line with a predefined focus width, and receiving an indication of a plurality of narrow-focused received lines in response to the transmitted at least one line,
code for creating a training dataset comprising a plurality of pairs of ultrasound imaging data capturing rapid motion of the certain tissue of at least one sample patient, wherein each pair of the plurality of pairs of ultrasound imaging data includes a single-line ultrasound imaging data captured based on at least one ultrasound transducer receiving a single line in response to a transmitted single narrow-focused pulse, and a multiple-line ultrasound imaging data captured based on at least one ultrasound transducer receiving a plurality of narrow-focused lines in response to simultaneously transmitted at least one line with predefined focus width; and
code for training a CNN according to the training data, for outputting a plurality of adjusted narrow-focused received lines according to an input of the indication of the plurality of narrow-focused received lines.

14. The system according to claim 13, wherein the at least one ultrasound transducer comprises a plurality of elements arranged as a phased array, wherein the CNN comprises a plurality of interpolation layers followed by an apodization layer comprising a convolutional layer for each of a plurality of channels corresponding to each of the plurality of elements, wherein the weights of each of the plurality of channels are initialized with a Hann window.

15. The system according to claim 13, wherein the CNN is trained by computing a discrepancy between the plurality of adjusted narrow-focused received lines computed by the CNN and the single-line imaging data denoting ground truth, and minimizing the discrepancy according to code for an optimizer.

16. The system according to claim 15, wherein the discrepancy is computed according to L1 norm training loss.

17. The system according to claim 13, wherein the single-line imaging data of each pair of the training dataset is obtained by ultrasound imaging of a sample individual, and the multi-line imaging data corresponding to the single-line imaging data denotes phantom data computed from the single-line imaging data by decimating the received pre-beamformed data.

18. The system according to claim 13, wherein the single-line imaging data of each pair of the training dataset is obtained by ultrasound imaging of a sample individual, and the multi-line imaging data corresponding to the single-line imaging data denotes phantom data computed from the single-line imaging data by summation of the received pre-beamformed data.

19. A method for imaging rapid motion of a certain tissue in a target patient, comprising:
activating at least one ultrasound transducer for simultaneously transmitting at least one line with a predefined focus width, and receiving from the at least one ultrasound transducer an indication of a plurality of narrow-focused received lines in response to the transmitted at least one line,
inputting the indication of the plurality of narrow-focused received lines into a convolutional neural network (CNN), wherein the CNN is trained on a training set comprising a plurality of pairs of ultrasound imaging data capturing rapid motion of the certain tissue of at least one sample patient, wherein each pair of the plurality of pairs of ultrasound imaging data includes a single-line ultrasound imaging data captured based on at least one ultrasound transducer receiving a single line in response to a transmitted single narrow-focused pulse, and a multiple-line ultrasound imaging data captured based on at least one ultrasound transducer receiving a plurality of narrow-focused lines in response to simultaneously transmitted at least one line with predefined focus width, and outputting by the CNN, a plurality of adjusted narrow-focused received line;
computing an adjusted ultrasound image according to the plurality of adjusted narrow-focused received lines; and
providing the adjusted ultrasound image for presentation on a display.

20. The method of claim 19, further comprising creating the training dataset; and training the CNN according to the training data.

* * * * *